United States Patent [19]

Pallos et al.

[11] Patent Number: 4,931,580
[45] Date of Patent: Jun. 5, 1990

[54] ARYL SULFONYLUREA CARBAMATES AND THIOLCARBAMATES AND SALTS THEREOF: HERBICIDAL ANTIDOTES

[76] Inventors: Ferenc M. Pallos, 136 Twin Peaks Dr., Walnut Creek, Calif. 94598; Kang-Chi Lin, 7458 Terrace Dr., El Cerrito, Calif. 94530; Laddie L. Green, 4345 Sherbourne Dr., San Jose, Calif. 95124

[21] Appl. No.: 564,981

[22] Filed: Dec. 23, 1983

Related U.S. Application Data

[63] Continuation of Ser. No. 312,251, Oct. 19, 1981, abandoned, which is a continuation-in-part of Ser. No. 207,991, Nov. 19, 1980, abandoned.

[51] Int. Cl.$^5$ ............................................. C07C 147/13
[52] U.S. Cl. ...................................... 560/13; 71/100; 71/103; 71/88; 71/94; 71/95; 71/118; 71/111; 558/233; 544/110
[58] Field of Search .......................................... 560/13

[56] References Cited

U.S. PATENT DOCUMENTS

| | | | |
|---|---|---|---|
| 3,253,902 | 5/1966 | Munz et al. | 71/100 |
| 3,439,018 | 4/1969 | Brookes et al. | 260/471 |
| 3,539,641 | 11/1970 | Dietrich | 260/397.7 |
| 3,547,618 | 12/1970 | Speziale et al. | 71/103 |
| 3,799,760 | 3/1974 | Stephens | 71/103 |
| 3,823,007 | 7/1974 | Stephens | 71/103 |
| 4,168,152 | 9/1979 | Gaughan et al. | 71/93 |
| 4,230,874 | 10/1980 | Pallos et al. | 560/12 |
| 4,260,824 | 4/1981 | Gaughan | 564/42 |
| 4,334,911 | 6/1982 | Gaughan et al. | 71/93 |

Primary Examiner—Glennon H. Hollrah
Assistant Examiner—Eric J. Kraus
Attorney, Agent, or Firm—Denis A. Polyn

[57] ABSTRACT

Aryl sulfonylureas as new compositions and included in a two-part herbicide system comprising at least one or more thiolcarbamate, thiolcarbamate sulfoxide or haloacetanilide herbicide, and as the second part a nonphytotoxic antidotally effective amount of aryl sulfonylurea as an antidote therefor of the formula

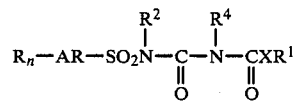

in which X is oxygen or sulfur; n is an integer; R is lower alkyl, lower alkoxy, lower alkylthio, halogen, trifluoromethyl, cyano, nitro, lower alkyl sulfonyl;

$R^4$ is hydrogen, lower alkyl, lower alkoxyalkyl, phenyl and chlorophenyl;

$R^2$ is hydrogen, lower alkyl, alkoxyalkyl and phenyl;

$R^1$ is lower alkyl, alkenyl, alkynyl, haloalkyl, alkoxyalkyl, 1-phenylpropenyl, benzyl, chlorobenzyl, haloalkenyl, phenyl and alkyl substituted phenyl; and AR is phenyl, benzyl, naphthyl, pyridyl or styryl; and the inorganic base salts sodium, potassium, ammonium and other inorganic salts; and organic base salts thereof.

37 Claims, No Drawings

ARYL SULFONYLUREA CARBAMATES AND THIOLCARBAMATES AND SALTS THEREOF: HERBICIDAL ANTIDOTES

CROSS REFERENCE TO RELATED APPLICATIONS

This is a continuation of application Ser. No. 312,251 filed Oct. 19, 1981 now abandoned which is a continuation-in-part of application Ser. No. 207,991, filed Nov. 19, 1980 now abandoned.

BACKGROUND OF THE INVENTION

While many herbicides are immediately toxic to a large number of weed pests, it is known that the effect of many herbicides upon important plant cultivations is either non-selective or not adequately selective. Thus, many herbicides damage not only the weeds to be controlled, but to a greater or lesser extent, the desirable cultivated plants as well. This holds true for many herbicidal compounds which have been commercially successful and are commercially available. These herbicides include types such as triazines, urea derivatives, halogenated acetanilides, carbamates, thiolcarbamates, thiolcarbamate sulfoxides, pyrrolidinones, and the like. Some examples of these compounds are described in U.S. Pat. Nos. 2,891,855, 2,913,237, 3,037,853, 3,175,897, 3,185,720, 3,198,786, 3,442,945, 3,582,314, 3,780,090, 3,952,056 and 4,110,105.

The side effect of injury to a cultivated crop by various herbicides is particularly inconvenient and unfortunate. When used in the recommended amounts in the soil to control broadleaf weeds and grasses, injury such as serious malformation or stunting of the crop plants results in loss of crop yield. The search continues for good selective herbicides.

Previous attempts are descrbed to overcome this problem. The treatment of the crop seed with certain "hormonal" antagonistic agents to planting is described, see U.S. Pat. Nos. 3,131,509 and 3,564,768. The protective agents, as well as the herbicide, in these prior processes are largely specific to certain cultivated plant species or in the nature of the antagonistic agents. The prior antagonistic agents have not been notably successful. The aforementioned patents specifically exemplify and describe the treatment of seeds employing compounds of a different chemical class not suggestive of the present invention.

DESCRIPTION OF THE INVENTION

It has been discovered that cultivated crop plants can be protected against injury by thiolcarbamate-type herbicides, thiolcarbamate sulfoxide-type herbicides, or haloacetanilide-type herbicides and the like, and said injury can be decreased when the thiolcarbamate-type herbicides, thiocarbamate sulfoxide-type herbicides or haloacetanilide-type herbicides each alone or in mixtures or combination with other compounds, are applied in a variety of ways. Further, as an alternative effect, the tolerance of the crop plants to these herbicides, can be substantially increased by adding to the soil an antidote compound of the type-aryl sulfonylureas.

Therefore, the present invention also includes a two-part herbicide system consisting essentially of a first-part of one or more herbicides heretofore mentioned, and a second-part of an effective antidote compound therefore, said antidote compounds corresponding to the following formula

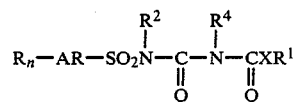

in which X is oxygen or sulfur; n is an integer 0 to 3 inclusive;

R is lower alkyl having 1 to 4 carbon atoms, inclusive, lower alkoxy having 1 to 4 carbon atoms, inclusive, lower alkylthio having 1 to 4 carbon atoms, inclusive, halogen, trifluoromethyl, cyano, nitro and lower alkyl sulfonyl;

$R^4$ is hydrogen and lower alkyl having 1 to 4 carbon atoms, inclusive, lower alkoxyalkyl having 2 to 6 carbon atoms, inclusive, phenyl and chlorophenyl;

$R^2$ is hydrogen, lower alkyl having 1 to 4 carbon atoms, alkoxyalkyl having 2-6 carbon atoms, and phenyl;

$R^1$ is lower alkyl having 1 to 4 carbon atoms, inclusive, alkenyl having 3 to 6 carbon atoms, inclusive; alkynyl having 3 to 6 carbon atoms, inclusive, haloalkyl having 1 to 4 carbon atoms, inclusive, alkoxyalkyl having 2 to 6 carbon atoms, inclusive, 1-phenyl propenyl, benzyl, chlorobenzyl, haloalkenyl having 3 to 6 carbon atoms inclusive, phenyl and alkyl substituted phenyl wherein the alkyl moiety has 1 to 4 carbon atoms, inclusive; and AR is phenyl, benzyl, naphthyl or pyridyl or styryl; and the inorganic base salts sodium, potassium, ammonium and other inorganic salts and organic base salts thereof selected from the group aniline, p-toluidine, benzylamine, allylamine, diallylamine, triallylamine, alkylamine, dialkylamine, trialkylamine, tetraalkyl ammonium, ethyl aminoethyl, alkanolamine, dialkanolamine, trialkanolamine, quinoline, isoquinoline, ethylenediamine, benzyltriallyl ammonium, choline, hydrazine, N,N-dialkyl hydrazine, morpholine and tribenzylamine.

By the terms "salt" or "salts thereof", it is meant those resulting compounds from the reaction of a compound of this invention and an inorganic or organic base. Inorganic bases include sodium hydroxide, sodium carbonate, potassium carbonate, potassium hydroxide, ammonium hydroxide, phosphonium or sulfonium bases and the like in water, or methanol or ethanol solvents. Organic bases include among others trialkylamines, dibenzylamines, quaternary organic bases, substituted ammonium bases, oxonium bases, other amines including alkyl substituted, alkanol substituted, alkenyl substituted, benzyl substituted, mixed-benzylalkyl substituted diamines, cholines, ammoniums, quinoline, morpholine, hydrazine, and substituted hydrazine, and the like.

It is recognized that the compounds of this invention have several "acidic" sites for reaction with an inorganic or organic base. Throughout the balance of the application the general nomenclature has been adopted for the sulfonamide salt, for example

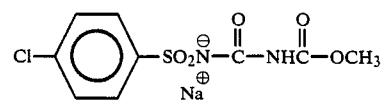

or carbamic acid or carbonic acid salt, for example

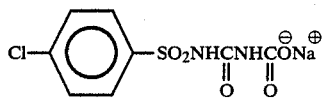

Also recognized is the fact that by using a 2:1 molar equivalent ratio of base to sulfonyl urea a combined or double salt sulfonamide salt and carbamic acid or carbonic acid salt is possible, such as

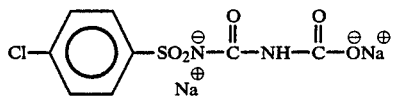

By way of exemplification, the active thiolcarbamate herbicides employed in the invention may include the following: EPTC, S-ethyl diisobutyl thiolcarbamate, S-propyl dipropyl thiolcarbamate, S-2,3,3,-trichloroallyl diisopropyl thiolcarbamate, S-ethyl cyclohexyl ethyl thiolcarbamate, S-ethyl hexahydro-1H-azepine-1-carbothioate, S-4-chlorobenzyl diethyl thiolcarbamate and combinations thereof.

The terms "lower alkyl" and "alkyl" include straight chain and branched chain and cyclic substituents of this group; for example, methyl, ethyl, n-propyl, isopropyl, n-butyl, isobutyl, pentyl, isopentyl, sec-pentyl, tert-butyl, n-hexyl, isohexyl, cyclopropyl, cyclobutyl, cyclohexyl, and the like; the term "lower alkoxy" includes straight chain and branched chain substituents of this group; for example, methoxy, ethoxy, n-propoxy, isopropoxy, n-butoxy, isobutoxy, pentoxy, isopentoxy, sec-butoxy, sec-pentoxy, tert-butoxy, n-hexoxy, isohexoxy and the like; the term "alkynyl" includes substituents of this type having straight or branched chain and at least one triple bond; for example, 1-propynyl, 2-propynyl, 1-butynyl, 2-butynyl, 1-hexynyl, 3-hexynyl and the like; and the term "alkenyl" includes substituents of this group having a straight or branched chain configuration and at least one double bond; for example, allyl, methallyl, ethallyl, 1-butenyl, 2-butenyl, 3-butenyl, 2-methyl-1-butenyl, 2-methyl-3-butenyl, 1-pentenyl, 2-pentenyl, 2-methyl-1-pentenyl and the like. The term "halo" includes those substituents as, chloro, bromo, iodo and fluoro as mono, di, tri or tetra substituents and combinations thereof.

By thiolcarbamate herbicides the present invention includes compounds of the formula

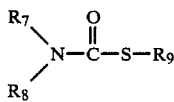

in which $R_7$ is selected from the group consisting of alkyl 1 to 6 carbon atoms and alkenyl 2 to 6 carbon atoms;

$R_8$ is selected from the group consisting of alkyl 1 to 6 carbon atoms, alkenyl 2 to 6 carbon atoms, cyclohexyl, phenyl and benzyl; or $R_7$ and $R_8$ taken together with the nitrogen atom to which they are attached form an alkylene ring substituted and unsubstituted 2 to 9 carbon atoms; and $R_9$ is selected from the group consisting of alkyl 1 to 6 carbon atoms, haloalkyl 1 to 6 carbon atoms, alkenylene ring 5 to 10 carbon atoms, phenyl, substituted phenyl, benzyl and substituted benzyl.

By thiolcarbamate sulfoxide-type herbicides are those thiolcarbamate herbicides mentioned herein which have been oxidized by methods as disclosed and described in U.S. Pat. Nos. 3,897,492, 3,986,168, 3,896,169 and 3,989,684 and which are incorporated herein by reference.

By way of exemplification, active thiolcarbamate sulfoxide herbicides employed in the present invention may include the following: S-ethyl dipropyl thiolcarbamate sulfoxide, S-ethyl diisobutyl thiolcarbamate sulfoxide, S-propyl dipropyl thiolcarbamate sulfoxide, S-2,3,3-trichloroalkyl diisopropyl thiolcarbamate sulfoxide, S-ethyl hexahydro-1H-azepine-1-carbothioate sulfoxide, S-4-chlorobenzyl diethyl thiolcarbamate sulfoxide and combinations thereof.

By haloacetanilide herbicides the present invention includes compounds of the formula

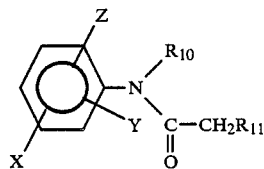

in which

X, Y and Z are independently selected from the group consisting of hydrogen, alkyl 1 to 4 carbon atoms and alkoxy 1 to 4 carbon atoms;

$R_{10}$ is selected from the group consisting of alkyl 1 to 6 carbon atoms, alkylalkoxy 2 to 10 carbon atoms, acetoxy 2 to 6 carbon atoms and dioxane; and $R_{11}$ is selected from the group consisting of chlorine, bromine and iodine.

By way of exemplification, active haloacetanilide herbicides employed in the invention may include the following: 2-chloro-2',6'-diethyl-N-(methoxymethyl) acetanilide, 2-chloro-2'-methyl,6'-ethyl-N-(methoxypropyl)-(2) acetanilide, 2-chloro-2',6'-dimethyl-N-(methoxymethyl) acetanilide, 2-chloro-2'methyl,6'-ethyl-N-(ethoxymethyl) acetanilide, 2-chloro-N-isopropyl acetanilide, 2-chloro-2',6'-diethyl-N-(n-butoxymethyl) acetanilide, and 2-chloro-N-carbethoxymethyl-2',6'-diethyl acetanilide.

In general, the active antidote compounds of the present invention can be prepared by the following methods.

I. An appropriate substituted aryl sulfonamide (1) is reacted with a substituted carbamoyl or thiocarbamoyl isocyanate (2) to produce the substituted aryl sulfonylurea (3). This reaction is depicted by the following equation:

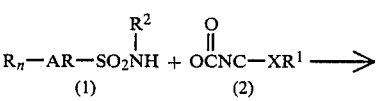

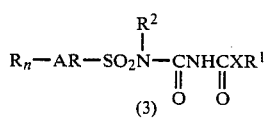

II. An alternative reaction is the reaction of a substituted carbamate or thiolcarbamate (4) with a substituted aryl sulfonyl isocyanate (5) to produce the substituted aryl sulfonylurea (6). This reaction is depicted by the following equation:

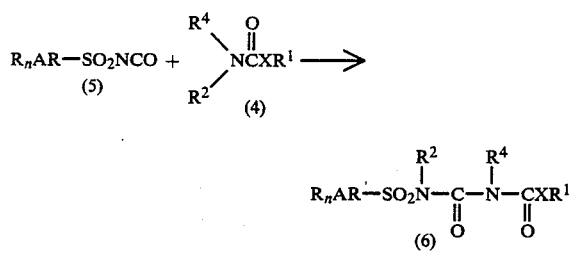

wherein R, AR, $R^1$ and n have the same significance as previously defined.

In reaction schemes I and II, the starting material intermediates are well-known in the prior art and the reactions described in I and II are performed in the presence of an organic solvent, such as toluene and the like, where good chemical practice dictates. The reactions are either exothermic as in II or heat can be applied as in I. The reaction temperatures can vary between about −20° C. to about 150° C. or the reflux temperature of the reaction mixture. The reaction pressure may be atmospheric, subatmospheric or superatmospheric. However, for convenience of conducting the reactions, the pressure is generally atmospheric. The reaction time will, of course vary depending upon the reactants and reaction temperature. Generally, the reaction time is from 0.25 to 24 hours depending upon the steps and rate of reaction. After the reaction is complete, the product is recovered by separation from the by-products and the solvent removed, as by filtration or evaporation or distillation. The structure is confirmed by nuclear magnetic resonance or infrared spectroscopy.

The compounds of the present invention and their preparation are more particularly illustrated by the following examples. Following the examples of preparation is a table of compounds which are prepared according to the procedures described herein. Compound numbers have been assigned to them and are used for identification throughout the balance of the specification.

EXAMPLE 1

Preparation of 1-(4'-chlorobenzenesulfonyl)-3-methoxycarbonyl urea

Methyl carbamate (43.0 grams, 0.57 moles) was stirred in 500 milliliters of dry toluene. 4-chlorobenzenesulfonyl isocyanate (125 grams, 0.57 moles) was added dropwise. An exothermic reaction occurred. The reaction mixture was kept at 80° C. for 1½hours. It was then cooled and the percipitate removed by filtration. The filtered material was washed with toluene and dried. There was obtained 159 grams of the title product, m.p. 174°–175° C.

EXAMPLE 2

Preparation of 1-(4'-nitrobenzenesulfonyl)-3-methoxycarbonyl urea

To 4-nitrobenzenesulfonamide (2.1 grams, 0.01 mole) in 100 milliliters dry toluene was added 1.2 grams (0.012 mole) methoxycarbonyl isocyanate. Three drops of pyridine were added. The mixture was refluxed for four hours. After cooling the precipitate was filtered off and washed with toluene. The solid material was dried. There was obtained 2.4 grams of the title compound, m.p. 150°–158° C.

EXAMPLE 3

Preparation of salts

Sodium salts of 1-(4'-chlorobenzenesulfonyl)-3-methoxy carbonyl urea

A. One equivalent weight of sodium hydroxide was added to one equivalent weight of 1-(4'-chlorobenzenesulfonyl)-3-methoxy carbonyl urea in aqueous solution. There was obtained at room temperature the monosodium carbamic acid salt of the starting compound.

B. One mole of 1-(4'-chlorobenzenesulfonyl)-3-methoxy carbonyl urea was added to one mole of sodium hydroxide in 5% methanol solution. This was stirred while cooling in an ice-water bath. The solvent was evaporated. There was obtained a white crystalline product, the sodium sulfonamide salt of the starting compound, m.p. 220°–221° C.

C. In a similar manner as B potassium hydroxide in methanol was reacted with 1-(4'-chlorobenzenesulfonyl)-3-methoxy carbonyl urea. The potassium sulfonamide salt was prepared and isolated, m.p. 75°–85° C.

D. In a similar manner as B, triethylamine in methanol was reacted with the compound from Example 1. The triethylamine sulfonamide salt was prepared and isolated, m.p. 100°–113° C.

E. In a similar manner as B, ammonium hydroxide in methanol was reacted with the compound from Example 1. The ammonium sulfonamide salt was prepared and isolated, m.p. 92°–98° C.

TABLE I

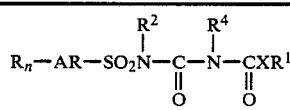

| Com. No. | $R_n$ | AR | $R^4$ | X | $R^1$ | $R_2$ | Physical Constant m.p. or $n_D^{30}$ |
|---|---|---|---|---|---|---|---|
| 1 | 4-Cl | phenyl | H | S | n-$C_4H_9$ | H | 88–92° C. |
| 2 | — | phenyl | H | O | $CH_3$ | H | semi-solid* |
| 3 | 4-Cl | phenyl | H | O | $CH_3$ | H | 174–175° C. |
| 4 | 4-Cl | phenyl | H | O | $C_2H_5$ | H | 104–107° C. |
| 5 | 4-Cl | phenyl | H | O | t-$C_4H_9$ | H | 96–100° C. |
| 6 | 4-Cl | phenyl | H | O | i-$C_3H_7$ | H | 82–95° C. |
| 7 | 4-$CH_3$ | phenyl | H | O | $CH_3$ | H | 138–140° C. |
| 8 | 4-$CH_3$ | phenyl | H | O | $C_2H_5$ | H | 156–157 |
| 9 | 4-$CH_3$ | phenyl | H | O | i-$C_3H_7$ | H | 140–142° C. |

TABLE I-continued $$R_n-AR-SO_2N-\underset{\underset{O}{\|}}{\overset{\overset{R^2}{|}}{C}}-N-\underset{\underset{O}{\|}}{\overset{\overset{R^4}{|}}{C}}XR^1$$

| Com. No. | $R_n$ | AR | $R^4$ | X | $R^1$ | $R_2$ | Physical Constant m.p. or $n_D^{30}$ |
|---|---|---|---|---|---|---|---|
| 10 | 4-CH₃ | phenyl | H | O | t-C₄H₉ | H | 123–125° C. |
| 11 | 3-CF₃ | phenyl | H | O | CH₃ | H | waxy-solid* |
| 12 | 2,5-diCl | phenyl | H | O | CH₃ | H | 123–133° C. |
| 13 | — | 2-pyridyl | H | O | CH₃ | H | 183–185° C. |
| 14 | — | 2-naphthyl | H | O | CH₃ | H | 154–164° C. |
| 15 | 2-Cl | phenyl | H | O | CH₃ | H | semi-solid* |
| 16 | 3-NO₂ | phenyl | H | O | CH₃ | H | 151–154° C. |
| 17 | 4-NO₂ | phenyl | H | O | CH₃ | H | 150–158° C. |
| 18 | 4-CH₃S | phenyl | H | O | CH₃ | H | 147–155° C. |
| 19 | 4-CH₃O | phenyl | H | O | CH₃ | H | 155–158° C. |
| 20 | 2-CH₃ | phenyl | H | O | CH₃ | H | 137–142° C. |
| 21 | 4-CH₃SO₂ | phenyl | H | O | CH₃ | H | semi-solid* |
| 22 | — | benzyl | H | O | CH₃ | H | 155–160° C. |
| 23 | 4-CH₃ | phenyl | CH₃ | O | CH₃ | H | 104–113° C. |
| 24 | 4-Cl | phenyl | CH₃ | O | CH₃ | H | 128–133° C. |
| 25 | 4-CH₃ | phenyl | C₂H₅ | O | CH₃ | H | 101–107° C. |
| 26 | 4-Cl | phenyl | C₂H₅ | O | CH₃ | H | 75–95° C. |
| 27 | 4-Cl | phenyl | H | O | CH₃ | sulfonamide sodium salt solution | 130–135° C. |
| 28 | 4-Cl | phenyl | H | O | CH₃ | sulfonamide sodium salt | 220–221° C. |
| 29 | 4-Cl | phenyl | H | O | Na⁺ Double salt | H | >300° C. |
| 30 | 4-Cl | phenyl | H | O | CH₃ | sulfonamide potassium salt | 75–85° C. |
| 31 | 4-Cl | phenyl | H | O | CH₃ | sulfonamide triethylamine salt | 100–113° C. |
| 32 | 4-Cl | phenyl | H | O | CH₃ | sulfonamide ammonium salt | 92–98° C. |
| 33 | 4-Cl | phenyl | H | O | CH₃ | sulfonamide tributylamine salt | viscous liquid |
| 34 | 4-Cl | phenyl | H | O | CH₃ | sulfonamide dibenzylamine salt | 145–150° C. |
| 35 | 4-Cl | phenyl | H | O | Na⁺ | carbamic acid sodium salt | |
| 36 | 4-Cl | phenyl | H | S | CH₃ | H | 171–181° C. |
| 37 | 4-CH₃ | phenyl | H | S | CH₃ | H | 181–187° C. |
| 38 | 2,5-diCH₃ | phenyl | H | O | CH₃ | H | 115–125° C. |
| 39 | 3,4-diCl | phenyl | H | O | CH₃ | H | 164–168° C. |
| 40 | 2-NO₂ | phenyl | H | O | CH₃ | H | 143–159° C. |
| 41 | 4-Br | phenyl | H | O | CH₃ | H | 181–187° C. |
| 42 | 3,5-diCl | phenyl | H | O | CH₃ | H | 194–195° C. |
| 43 | 4-F | phenyl | H | O | CH₃ | H | 157–160° C. |
| 44 | 3-Cl | phenyl | H | O | CH₃ | H | 140–141° C. |
| 45 | 4-NO₂ | phenyl | H | O | CH₃OCH₂CH₂— | H | 130–134° C. |
| 46 | 4-CH₃ | phenyl | H | O | CH₃ | H | semi-solid* |
| 47 | 4-Cl | phenyl | H | O | CH₃OCH₂CH₂— | H | semi-solid* |
| 48 | 4-CH₃ | phenyl | H | O | benzyl | H | 165–169° C. |
| 49 | 4-CH₃ | phenyl | H | O | CH₂=CHCH₂ | H | 126–130° C. |
| 50 | 4-Cl | phenyl | H | O | benzyl | H | 176–179° C. |
| 51 | 4-Cl | phenyl | H | O | CH₂=CHCH₂— | H | 122–125° C. |
| 52 | 4-NO₂ | phenyl | H | O | C₂H₅ | H | 183–185° C. |
| 53 | 4-NO₂ | phenyl | C₂H₅ | O | CH₃ | H | 128–131° C. |
| 54 | 4-Cl | phenyl | i-C₃H₇ | O | CH₃ | H | 85–92° C. |
| 55 | 4-Cl | phenyl | n-C₃H₇ | O | CH₃ | H | semi-solid* |
| 56 | 4-Cl | phenyl | phenyl | O | CH₃ | H | semi-solid* |
| 57 | 4-Cl | phenyl | 4-Cl-phenyl | O | CH₃ | H | 123–129° C. |
| 58 | 4-Cl | phenyl | CH₃OCH₂CH₂ | O | CH₃ | H | liquid* |
| 59 | 4-NO₂ | phenyl | CH₃OCH₂CH₂ | O | CH₃ | H | liquid* |
| 60 | 4-Cl | phenyl | H | O | CH₃ | CH₃ | semi-solid* |
| 61 | 4-NO₂ | phenyl | H | O | CH₃ | phenyl | 107–110° C. |
| 62 | 4-Cl | phenyl | H | O | CH₃ | CH₃ | semi solid* |
| 63 | 4-CH₃ | phenyl | H | O | CH≡CCH₂— | H | 155–158° C. |
| 64 | 4-CH₃ | phenyl | H | O | CH₃C≡CCH₂— | H | 147–154° C. |
| 65 | 4-Cl | phenyl | CH₃ | O | CF₃H₂— | H | 83–86° C. |
| 66 | 3-Cl | phenyl | H | O | C₂H₅ | H | 137–130° C. |
| 67 | 3-Cl | phenyl | H | O | i-C₃H₇ | H | 140–141° C. |
| 68 | 3-Cl | phenyl | H | O | (CH₃)₂CHCH— | H | 102–104° C. |
| 69 | 3-Cl | phenyl | H | O | CH₃OCH₂CH₂— | H | slurry* |
| 70 | 3-Cl | phenyl | H | O | (CH₂)₂OCH₂CH₂— | H | $n_D^{30} = 1.5084$ |
| 71 | 4-Cl | phenyl | C₂H₅ | S | CH₃ | H | semi-solid* |
| 72 | 4-NO₂ | phenyl | H | O | phenyl | H | 161–166° C. |

TABLE I-continued $$R_n-AR-SO_2\overset{R^2}{\underset{\|}{\underset{O}{N}}}-\overset{}{\underset{\|}{\underset{O}{C}}}-\overset{R^4}{N}-CXR^1$$

| Com. No. | $R_n$ | AR | $R^4$ | X | $R^1$ | $R_2$ | Physical Constant m.p. or $n_D^{30}$ |
|---|---|---|---|---|---|---|---|
| 73 | 4-CF$_3$ | phenyl | H | O | CH$_3$ | H | 158–159° C. |
| 74 | 4-CF$_3$ | phenyl | H | O | C$_2$H$_5$ | H | 152–153° C. |
| 75 | 4-CF$_3$ | phenyl | H | O | i-C$_3$H$_7$ | H | 160–161° C. |
| 76 | 4-CF$_3$ | phenyl | H | O | i-C$_4$H$_9$ | H | 150–152° C. |
| 77 | 4-NO$_2$ | phenyl | H | O | benzyl | H | 170–173° C. |
| 78 | 4-Cl | phenyl | H | O | CH$_3$ | CH$_3$OCH$_2$CH$_2$— | slurry |
| 79 | — | 1-naphthyl | H | O | CH$_3$ | H | 136–139° C. |
| 80 | 4-Cl | phenyl | H | O | CH$_3$C≡CCH$_2$— | H | 120–123° C. |
| 81 | 4-NO$_2$ | phenyl | H | O | CH$_2$=CHCH$_2$— | H | 158–162° C. |
| 82 | 4-NO$_2$ | phenyl | H | O | CH$_3$C≡CCH$_2$— | H | 170–172° C. |
| 83 | 4-CF$_3$ | phenyl | H | O | CH$_3$OCH$_2$CH$_3$ | H | 112–113° C. |
| 84 | 4-CF$_3$ | phenyl | H | O | i-C$_3$H$_7$OCH$_2$CH$_2$— | H | soft solid* |
| 85 | 4-Cl | phenyl | H | O | CH$_3$ | sulfonamide aniline salt | 79–82° C. |
| 86 | 4-Cl | phenyl | H | O | CH$_3$ | sulfonamide p-toluidine salt | 128–129° C. |
| 87 | 4-Cl | phenyl | H | O | CH$_3$ | sulfonamide benzylamine salt | 153–154° C. |
| 88 | 4-Cl | phenyl | H | O | CH$_3$ | sulfonamide allylamine salt | 154–155° C. |
| 89 | 4-Cl | phenyl | H | O | CH$_3$ | sulfonamide diallylamine salt | 118–121° C. |
| 90 | 4-Cl | phenyl | H | O | CH$_3$ | sulfonamide di-ethylamino propylamine salt | 134–136° C. |
| 91 | 4-Cl | phenyl | H | O | CH$_3$ | sulfonamide ethanol amine salt | 1.5421 |
| 92 | 4-Cl | phenyl | H | O | CH$_3$ | sulfonamide quinoline salt | 75–85° C. |
| 93 | 4-Cl | phenyl | H | O | CH$_3$ | sulfonamide triethanol-amine salt | 1.5410 |
| 94 | 4-Cl | phenyl | H | O | CH$_3$ | sulfonamide diethylamino ethanol salt | 1.5292 |
| 95 | 4-Cl | phenyl | H | O | CH$_3$ | sulfonamide methylamine salt | 152–154° C. |
| 96 | 4-Cl | phenyl | H | O | CH$_3$ | sulfonamide ethylamine salt | 126–128° C. |
| 97 | 4-Cl | phenyl | H | O | CH$_3$ | sulfonamide diethylamine salt | 54–61° C. |
| 98 | 4-Cl | phenyl | H | O | CH$_3$ | sulfonamide n-propylamine salt | 159–163° C. |
| 99 | 4-Cl | phenyl | H | O | CH$_3$ | sulfonamide i-propylamine salt | 104–108° C. |
| 100 | 4-Cl | phenyl | H | O | CH$_3$ | sulfonamide diisopropyl-amine salt | 128–131° C. |
| 101 | 4-Cl | phenyl | H | O | CH$_3$ | sulfonamide hydrazine salt | 72–78° C. |
| 102 | 4-Cl | phenyl | H | O | CH$_3$ | sulfonamide N,N-dimethyl hydrazine salt | 61–64° C. |
| 103 | 4-Cl | phenyl | H | O | CH$_3$ | sulfonamide ethylene diamine bis-salt | 184–186° C. |
| 104 | 4-Cl | phenyl | H | O | CH$_3$ | sulfonamide ethylamino ethyl amine salt | 69–76° C. |
| 105 | 4-Cl | phenyl | H | O | CH$_3$ | sulfonamide tetraethyl ammonium salt | 46–49° C. |
| 106 | 4-Cl | phenyl | H | O | CH$_3$ | sulfonamide | 99–102° C. |

TABLE I-continued $$R_n-AR-SO_2N-\underset{\underset{O}{\|}}{C}-N-\underset{\underset{O}{\|}}{C}XR^1$$
with $R^2$ on the first C-N and $R^4$ on the N.

| Com. No. | $R_n$ | AR | $R^4$ | X | $R^1$ | $R_2$ | Physical Constant m.p. or $n_D^{30}$ |
|---|---|---|---|---|---|---|---|
| 107 | 4-Cl | phenyl | H | O | CH₃ | tetrabutyl ammonium salt sulfonamide isoquinoline salt | 92–98° C. |
| 108 | 4-Cl | phenyl | H | O | CH₃ | sulfonamide diethanolamine salt | 42–47° C. |
| 109 | 4-Cl | phenyl | H | O | CH₃ | sulfonamide morpholine salt | 156–158° C. |
| 110 | 4-Cl | phenyl | H | O | CH₃ | sulfonamide tribenzylamine salt | 91–95° C. |
| 111 | 4-Cl | phenyl | H | O | CH₃ | sulfonamide choline salt | 1.5250 |
| 112 | 4-Cl | phenyl | H | O | CH₃ | sulfonamide hexadecyl trimethyl ammonium salt | 84–87° C. |
| 113 | 4-Cl | phenyl | H | O | CH₃ | sulfonamide benzyltrimethyl ammonium salt | semi-solid* |
| 114 | 4-Cl | phenyl | H | O | CH₃ | sulfonamide triethylphenyl ammonium salt | semi-solid* |
| 115 | 4-Cl | phenyl | H | O | CH≡CCH₂— | H | 135–140° C. |
| 116 | 4-Cl | phenyl | H | O | CH₃ | sulfonamide triallylamine salt | 1.5354 |
| 117 | 3-NO₂, 4-Cl | phenyl | H | O | CH₃ | H | 149–154° C. |
| 118 | 4-NO₂ | phenyl | CH₃ | O | CH₃ | H | 145–150° C. |
| 119 | 4-Cl | phenyl | CH₃ | O | CH₂=CHCH₂— | H | 64–66° C. |
| 120 | 4-Cl | phenyl | CH₃ | O | CH≡CCH₂ | H | 150–154° C. |
| 121 | 4-NO₂ | phenyl | CH₃ | O | CH₃ | H | 98–101° C. |
| 122 | 4-NO₂ | phenyl | CH₃ | O | C₂H₅ | H | 99–103° C. |
| 123 | 4-Cl | phenyl | CH₃ | O | C₂H₅ | H | 62–66° C. |
| 124 | 4-Cl | phenyl | C₂H₅ | O | C₂H₅ | H | 69–74° C. |
| 125 | 4-NO₂ | phenyl | C₂H₅ | O | C₂H₅ | H | 99–101° C. |
| 126 | 4-Cl | phenyl | CH₃ | O | CH₃C≡CCH₂— | H | 83–89° C. |
| 127 | 4-CH₃ | phenyl | CH₃ | O | benzyl | H | 84–91° C. |
| 128 | 4-CH₃ | phenyl | CH₃ | O | CH₂=CHCH₂— | H | 50–57° C. |
| 129 | 4-CH₃ | phenyl | CH₃ | O | CH≡CCH₂ | H | 154–158° C. |
| 130 | 4-CH₃ | phenyl | CH₃ | O | CH₃C≡CCH₂— | H | 100–110° C. |
| 131 | 4-NO₂ | phenyl | CH₃ | O | benzyl | H | 136–139° C. |
| 132 | 4-NO₂ | phenyl | H | O | CH₃ | sulfonamide choline salt | 52–58° C. |
| 133 | 4-CH₃ | phenyl | C₂H₅ | O | CH₂=CHCH₂— | H | 1.5258 |
| 134 | 4-CH₃ | phenyl | C₂H₅ | O | CH≡CCH₂— | H | 75–80° C. |
| 135 | 4-CH₃ | phenyl | C₂H₅ | O | CH₃C≡CCH₂ | H | 85–92° C. |
| 136 | 4-Cl | phenyl | C₂H₅ | O | CH₂=CHCH₂— | H | 1.5336 |
| 137 | 4-Cl | phenyl | C₂H₅ | O | CH≡CCH₂— | H | 95–100° C. |
| 138 | 4-Cl | phenyl | C₂H₅ | O | CH₃C≡CCH₂— | H | waxy-solid |
| 139 | 4-CH₃ | phenyl | H | O | CH₂=C(CH₃)CH₂— | H | 132–134° C. |
| 140 | 4-Cl | phenyl | CH₃ | O | CH₂=C(CH₃)CH₂— | H | 81–88° C. |
| 141 | 4-Cl | phenyl | H | O | CH₃CH=CHCH₂— | H | 72–77° C. |
| 142 | 4-CH₃ | phenyl | H | O | CH₂ClCH₂— | H | 118–121° C. |
| 143 | 4-Cl | phenyl | H | O | CH₂ClCH₂— | H | 102–112° C. |
| 144 | 4-CH₃ | phenyl | C₂H₅ | O | CH₂=C(CH₃)CH₂— | H | 1.5090 |
| 145 | 4-Cl | phenyl | H | O | CH₂=C(CH₃)CH₂— | H | 149–152° C. |
| 146 | 4-Cl | phenyl | —CH₂CH=CH₂ | O | CH₃ | H | 1.5388 |
| 147 | 4-CH₃ | phenyl | H | O | CH₃CH=CHCH₂— | H | 52–60° C. |
| 148 | 4-CH₃ | phenyl | CH₃ | O | (CH₃)₃CCH₂— | H | 94–97° C. |
| 149 | 4-CH₃ | phenyl | CH₃ | O | HC≡CCH(phenyl)- | H | 1.5533 |
| 150 | 4-CH₃ | phenyl | H | O | (CH₃)₃CCH₂— | H | 83–91° C. |
| 151 | 4-CH₃ | phenyl | C₂H₅ | O | (CH₃)₃CCH₂— | H | 102–106° C. |
| 152 | 4-CH₃ | phenyl | H | O | CH₂=C(Cl)CH₂— | H | 128–131° C. |
| 153 | 4-Cl | phenyl | H | O | CH₂=C(Cl)CH₂— | H | 128–133° C. |
| 154 | 4-Cl | phenyl | C₂H₅ | O | (CH₃)₃CCH₂— | H | 83–87° C. |
| 155 | 4-CH₃ | phenyl | CH₃ | O | CH₃CH=CHCH₂— | H | 1.5272 |
| 156 | 4-Cl | phenyl | H | O | (CH₃)₃CCH₂— | H | 97–103° C. |
| 157 | 4-Cl | phenyl | CH₃ | O | (CH₃)₃CCH₂— | H | 122–126° C. |

TABLE I-continued

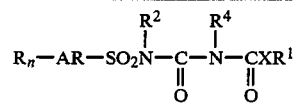

$$R_n-AR-SO_2\underset{\underset{O}{\|}}{N}-\underset{R^2}{\overset{|}{C}}-\underset{\underset{O}{\|}}{N}-\overset{R^4}{\overset{|}{C}}XR^1$$

| Com. No. | $R_n$ | AR | $R^4$ | X | $R^1$ | $R_2$ | Physical Constant m.p. or $n_D^{30}$ |
|---|---|---|---|---|---|---|---|
| 158 | 3-CH$_3$O, 4-Cl | phenyl | H | O | CH$_3$ | H | 160–164° C. |
| 159 | 2-CH$_3$O, 5-Cl | phenyl | H | O | CH$_3$ | H | 163–166° C. |
| 160 | — | styryl | H | O | CH$_3$ | H | 145–152° C. |
| 161 | 4-Cl | phenyl | CH$_3$ | O | CH≡CC(CH$_3$)$_2$— | H | 1.5262 |
| 162 | 4-Cl | phenyl | C$_2$H$_5$ | O | CH≡CC(CH$_3$)$_2$— | H | 1.5188 |
| 163 | 4-NO$_2$ | phenyl | CH$_3$ | O | CH$_2$=CHCH$_2$— | H | 94–97° C. |
| 164 | 4-NO$_2$ | phenyl | CH$_3$ | O | CH≡CCH$_2$— | H | 100–105° C. |

*Confirmed by nuclear magnetic resonance or infrared spectroscopy.

It is clear that the classes of herbicidal agents described and illustrated herein are characterized as effective herbicides exhibiting such activity. The degree of this herbicidal activity varies among specific compounds and among combinations of specific compounds within the classes. Similarly, the degree of activity to some extent varies among the species of plants to which a specific herbicidal compound or combination may be applied. Thus, selection of a specific herbicidal compound or combination to control undesirable plant species readily may be made. Within the present invention the prevention of injury to a desired crop species in the presence of a specific compound or combination may be achieved. The beneficial plant species which can be protected by this method is not intended to be limited by the specific crops employed in the examples.

The herbicidal compounds employed in the utility of this invention are active herbicides of a general type. That is, the members of the classes are herbicidally effective against a wide range of plant species with little or no discrimination between desirable and undesirable species. The method of controlling vegetation comprises applying an herbicidally effective amount of the herein described herbicidal compounds to the area or plant locus where control is desired.

An herbicide as used herein means a compound which controls or modifies the growth of vegetation or plants. Such controlling or modifying effects include all deviations from natural development; for example, killing, retardation, defoliation, desiccation, regulation, stunting, tillering, stimulation, dwarfing and the like. By "plants" it is meant germinant seeds, emerging seedlings, and established vegetation, including the roots and above-ground portions.

The terms "herbicide antidote" or "antidotal amount" are meant to describe the effect which tends to counteract the normal injurious herbicidal response that the herbicide might otherwise produce. Whether it is to be termed a remedy, interferant, protectant, or the like, will depend upon the exact mode of action. The mode of action is varied, but the effect, which is desirable, is the result of the method of treating the seed, soil or furrow in which a crop is planted. Hitherto, there have been no systems employing the antidote of the present invention which have been satisfactory for this purpose.

Broadly considered, this invention additionally relates to herbicidal compositions and methods comprising an active thiolcarbamate or haloacetanilide herbicide compound and a non-phytotoxic antidotally effective amount of a carbamate or thiolcarbamate or inorganic or organic salt of a combination or thiolcarbamate of an aryl sulfonylurea having 5 to 12 carbon atoms, inclusive, said carbamate, thiolcarbamate or salt thereof being antidotally active with said herbicide compound.

As alternative modes of action, the compounds of this invention may interfere with the normal herbicidal action of the thiolcarbamate-type, thiolcarbamate sulfoxide-type or haloacetanilide-type or other herbicides to render them selective in their action. The observation noted with the presence of the herein described antidote is a decrease in phytotoxicity with respect to various crops. The phytotoxicity is otherwise observed when various thiolcarbamates, thiolcarbamate sulfoxides or haloacetanilide herbicides are used for weed control. Whichever mode of action is present, the corresponding beneficial and desirable effect is the continued herbicidal effect of the thiolcarbamate, thiolcarbamate sulfoxide or haloacetanilide against weed species present with the crop, with the accompanying selective decreased herbicidal effect on desired crop species. This advantage and utility will become more apparent hereinafter.

Evaluation and Testing Procedure

Stock solutions of the herbicides were prepared by diluting the requisite amount of each herbicide in water. The solution compositions and application rates and methods are summarized in Table II.

Test Procedures and Results

TABLE II

| Herbicide Name | Herbicide Stock Solution Composition | | Application | | |
|---|---|---|---|---|---|
| | Herbicide (mg) | Water or Acetone (ml) | ml/flat | lb/acre | Method[1] |
| VERNAM ® | 296 | 400 | 5 | 1.0 | PPI |
| S-propyl N,N- | 370 | 370 | 5 | 1.25 | PPI |
| dipropyl thio- | 167 | 150 | 5 | 1.5 | PPI |

TABLE II-continued

| | Herbicide Stock Solution Composition | | Application | | |
|---|---|---|---|---|---|
| Herbicide Name | Herbicide (mg) | Water or Acetone (ml) | ml/flat | lb/acre | Method[1] |
| carbamate | 148 | 100 | 5 | 2.0 | PPI |
| | 370 | 200 | 5 | 2.5 | PPI |
| | 296 | 100 | 5 | 4 | PPI |
| | 1480 | 400 | 5 | 5 | PPI |
| | 1776 | 400 | | 6 | PPI |
| TILLAM ® S-propyl butyl-ethylthiocarbamate | 296 | 100 | 5 | 4 | PPI |
| RO-NEET ® S-ethyl N-cyclo-hexyl-N-ethyl thio-carbamate | 740 | 250 | 5 | 3 | PPI |
| SUTAN ® S-ethyl diisobutyl-thiocarbamate | 2960 | 500 | 5 | 3 | PPI |
| LASSO ® 2-chloro-2'-6'-diethyl-N-(methoxy-methyl) acetanilide | 7656 | 700 (1:1)[3] | L.S.T.[2] | 2.5 | PES |
| TERIDOX ® 2-chloro 2'-methyl-N-(methoxyethyl) acet-anilide | 1050 | 700 (1:1)[3] | L.S.T.[2] | 1 | PES |
| HERBICIDE A S-isobutyl N,N-diethylthiocarbamate | 148 222 | 50 50 | 5 5 | 4 6 | PPI PPI |
| HERBICIDE B S-butyl isobutyl-ethylthiocarbamate | 296 284 | 100 50 | 5 5 | 4 6 | PPI PPI |
| HERBICIDE C S-butyl propyliso-propylthiocarbamate | 296 222 | 100 50 | 5 5 | 4 6 | PPI PPI |
| HERBICIDE D 2-t-butyl,6-methyl-N-n-propoxymethyl-chloroacetanilide | 37 | 20 | 2 | 1 | PES |
| HERBICIDE E 2-t-butyl,6-methyl-N-ethoxymethyl-chloroacetanilide | 37 | 20 | 2 | 1 | PES |
| HERBICIDE F S-propyl N,N-diiso-butylthiocarbamate | 111 | 50 | 5 | 1 | PPI |
| HERBICIDE G S-butyl N,N-diiso-butylthiocarbamate sulfoxide | 111 | 50 | 5 | 3 | PPI |

[1] Method
PES = Pre-emergence surface application
PPI = Pre-plant incorporation
[2] L.S.T. = Linear spray table
[3] = (Water:acetone)

Stock solutions of each antidote compound were prepared at the desired concentration by diluting the requisite amounts of each antidote in acetone. The compositions and rates for each method of application are summarized in Table III.

TABLE III

| Antidote Stock Solutions Antidote: Aryl Sulfonylureas | | | | |
|---|---|---|---|---|
| Composition | | Application | | |
| Antidote (mg) | Acetone (ml) | ml/flat | lb/acre | Method[1] |
| 93 | 15 | 0.3 | 1.0 | IF |
| 93 | 15 | 1.5 | 5.0 | IF |
| 37 | 100 | 5.0 | 0.5 | PPI |
| 74 | 100 | 5.0 | 1.0 | PPI |
| 148 | 100 | 5.0 | 2.0 | PPI |
| 93 | 25 | 5.0 | 5.0 | PPI |
| 16 | 5 | ½ ml/10 grams seed | 0.015 | ST |
| 16 | 2.5 | ½ ml/10 grams seed | 0.03 | ST |
| 50 | 4 | ½ ml/10 grams seed | 0.06 | ST |
| 100 | 4 | ½ ml/10 grams seed | 0.125 | ST |
| 25 | ½ | ½ ml/10 grams seed | 0.25 | ST |
| 200 | 2 | ½ ml/10 grams seed | 0.5 | ST |

IF = In-furrow surface application
PPI = Pre-plant incorporation of herbicide and antidote as a tank mix
ST = Seed treatment All of the soil used in the tests described herein was loamy sand soil treated with 50 parts per million (ppm) each of a commercially available fungicide, cis-N[trichloromethyl)-thio]-4-cyclohexene-1,2-dicarboximide, and 18—18—18 fertilizer, which contains 18% by weight equivalent each of nitrogen, phosphorus pentoxide, and potassium oxide.

The thiocarbamate herbicides were applied to the soil by preplant incorporation (PPI) either alone or with the antidote as a tank mix. The acetanilide and pyrrolidinone herbicides were applied by atomizing the herbicide, or herbicide/antidote tank mix, to the soil surface of seeded flats.

The antidote compounds were applied by PPI, pre-emergence surface (PES), seed treatment (ST), and in-furrow (IF) methods of application.

For in-furrow antidote applications, a one pint (473 cubic centimeters) sample of soil from each planting flat was removed and retained. After leveling and furrowing the soil, seeds of the crop or weed species were planted ½ inch (1.27 centimeter). Each flat was divided in half by a wooden barrier. A stock solution of the antidote was atomized directly onto the exposed seeds and soil in the open furrow on one side of the barrier. The seeds in the entire flat were then covered with the previously removed soil. The antidotally untreated sections of flats were compared for observed differences which would indicate lateral movement of the antidote through the soil.

For the pre-plant incorporation method the herbicide and the antidote of each test group were incorporated into the soil either each alone or together as a tank mix using a five gallon rotary mixer.

Pre-emergence surface (PES) application involves spraying the soil-covered seeds after planting.

All flats were placed on greenhouse benches where temperature was maintained between 70° and 90° F. (21° to about 32° C.). The flats were watered by sprinkling as needed to assure good plant growth.

Control flats contained crops treated with herbicides only at the various rates and method of application.

Injury ratings were taken four weeks after application of the antidote. The effectiveness of the antidote was determined by visual comparison of injuries to crops and weeds in the control and test flats to those in untreated flats.

The treated crops initially screened for diminution of herbicidal injury were milo (MO), wheat (WH), cotton (CT), rice (RC), barley (BA), corn (CN) and soybeans (SOY). Those compounds which showed substantial crop injury reduction were further tested at reduced rates. The herbicides and antidote compositions were then screened on at least two weed species. The weed species tested for control included watergrass (WG) (*Echinochloa crusgalli*), foxtail (FT) (*Setaria virdis*), wild oats (WO) (*Avena fatua*), shattercane (SC) (*Sorghum bicolor*), Johnsongrass (JG) (*Sorghum halepense*), wild oats (WO) (*Avena fatua*), nutsedge (NS) (*Cyperus esculentus*), crabgrass (CG) (*Digitaria sanguinalis*), (L.) Scop, mustard (MD) (*Brassica juncea*), signalgrass (SG) (*Brachiaria platyphylla*), and cockleburr (CB) (*Xanthium pensylvanicum*).

TABLE IV

| Compound Number | Antidote Rate & Method | Herbicide Rate & Method | Crop | Result | Weed | Result |
|---|---|---|---|---|---|---|
| 1 | 5 IF | 1 PPI VERNAM | CT | 40/60 | | |
| | | | BA | 50/70 | | |
| | 5 IF | 6 PPI VERNAM | SOY | 40/60 | | |
| | 1 IF | 6 PPI VERNAM | SOY | 30/45 | FT | 100/100 |
| | | | | | CG | 95/95 |
| | 5 IF | 6 PPI VERNAM | SOY | 10/45 | FT | 100/100 |
| | | | | | CG | 95/95 |
| 2 | 5 IF | 1 PPI VERNAM | BA | 40/60 | | |
| | 5 IF | 6 PPI VERNAM | SOY | 0/50 | | |
| | 1 IF | 6 PPI VERNAM | SOY | 20/40 | WG | 100/100 |
| | | | | | FT | 100/100 |
| | 2 PPI-TM | 6 PPI VERNAM | SOY | 40/65 | WG | 100/100 |
| | | | | | FT | 100/100 |
| 3 | 5 IF | 1¼ PPI VERNAM | MO | 40/100 | | |
| | 5 IF | 6 PPI VERNAM | CN | 50/90 | | |
| | 1 IF | 3 PPI RO-NEET | MO | 40/75 | FT | 80/80 |
| | | | | | SC | 95/95 |
| | 5 PPI-TM | 6 PPI VERNAM | SOY | 15/60 | WG | 100/100 |
| | | | | | FT | 100/100 |
| 3 | 1 PPI-TM | 6 PPI VERNAM | SOY | 0/60 | WG | 100/100 |
| | | | | | FT | 100/100 |
| | 5 IF | 3½ PES LASSO | MO | 45/95 | WG | 100/100 |
| | | | RC | 70/100 | | |
| | | | BA | 60/70 | | |
| | 5 IF | 1 PES TERIDOX | MO | 35/100 | WG | 100/100 |
| | | | WH | 60/70 | | |
| | | | BA | 60/80 | | |
| | | | CN | 85/100 | | |
| | .125 ST | 5 PPI VERNAM | SOY | 10/40 | WG | 100/100 |
| | 5 PPI-TM | 6 PPI VERNAM | SOY | 35/70 | WG | 100/100 |
| | 5 PPI-TM | 4 PPI VERNAM | SOY | 10/60 | WG | 100/100 |
| | .015% ST | 2.5 PPI VERNAM | SOY | 20/40 | | |
| | 5 IF | 3 PPI RO-NEET | MO | 40/75 | WG | 95/95 |
| | | | | | FT | 95/95 |
| | 2.0 PPI-TM | 6 PPI A | SOY | 10/45 | | |
| | .5 PPI-TM | 4 PPI B | SOY | 0/35 | WG | 75/75 |
| | .5 PPI-TM | 6 PPI C | SOY | 0/15 | WG | 95/95 |
| | .3 PPI-TM | 3 PPI F | SOY | 0/30 | WG | 100/100 |
| | 1 PPI-TM | 3 PPI F | SOY | 0/30 | WG | 100/100 |
| | 2 PPI-TM | 3 PPI F | SOY | 0/30 | WG | 100/100 |
| | 1 PPI-TM | 3 PPI G | SOY | 0/10 | WG | 100/100 |
| | .5 PES-TM | 1 PES D | SOY | 0/15 | WG | 100/100 |
| | 2 PES-TM | 1 PES E | SOY | 10/25 | WG | 100/100 |
| | .5 PPI-TM | 4 PPI TILLAM | SOY | 0/47 | WG | 95/95 |
| | 1 PPI-TM | 4 PPI TILLAM | SOY | 0/47 | WG | 95/95 |

TABLE IV-continued

| Compound Number | Antidote Rate & Method | Herbicide Rate & Method | Crop | Result | Weed | Result |
|---|---|---|---|---|---|---|
| 4 | 5 IF | 1¼ PPI VERNAM | BA | 50/90 | | |
| | 5 IF | 6 PPI VERNAM | SOY | 20/50 | | |
| | 5 IF | 3 PPI RO-NEET | MO | 40/75 | FT | 80/80 |
| | | | | | SC | 95/95 |
| | 5 PPI-TM | 6 PPI VERNAM | SOY | 35/70 | WG | 100/100 |
| | 5 IF | 3 PPI RO-NEET | MO | 45/75 | WG | 100/100 |
| | | | | | FT | 100/100 |
| 5 | 5 IF | 1¼ PPI VERNAM | MO | 60/100 | | |
| | 1 IF | 3 PPI RO-NEET | MO | 45/75 | WG | 95/95 |
| | | | | | FT | 95/95 |
| 6 | 5 IF | 6 PPI VERNAM | CN | 40/90 | | |
| | 5 PPI-TM | 6 PPI VERNAM | SOY | 45/70 | WG | 100/100 |
| | | | | | FT | 97/97 |
| | 5 IF | 3.5 PES LASSO | MO | 40/95 | WG | 100/100 |
| | | | WH | 55/70 | | |
| | | | BA | 55/70 | | |
| | 5 IF | 3 PPI RO-NEET | MO | 35/75 | WG | 95/95 |
| | | | | | FT | 95/95 |
| 7 | 5 IF | 1¼ PPI VERNAM | WH | 50/85 | | |
| | 5 IF | 6 PPI VERNAM | CN | 60/90 | | |
| 8 | 5 IF | 6 PPI VERNAM | CN | 70/90 | | |
| | | | SOY | 40/60 | | |
| | 1 IF | 5 PPI VERNAM | SOY | 20/60 | WG | 100/100 |
| | | | | | FT | 90/90 |
| 9 | 5 IF | 6 PPI VERNAM | CN | 50/90 | | |
| | 5 PPI-TM | 6 PPI VERNAM | SOY | 55/70 | WG | 100/100 |
| | 5 IF | 3 PPI RO-NEET | MO | 30/75 | WG | 85/95 |
| | | | | | FT | 95/95 |
| 10 | 1 PPI-TM | 6 PPI SUTAN | CT | 10/50 | NS | 90/90 |
| | | | | | JG | 100/100 |
| | 1 PPI-TM | 1¼ PPI VERNAM | CT | 20/30 | WG | 100/100 |
| | | | | | FT | 100/100 |
| 11 | 5 IF | 6 PPI VERNAM | CN | 20/90 | | |
| | 2 PPI-TM | 4 PPI VERNAM | SOY | 25/60 | WG | 100/100 |
| 12 | 5 IF | 1¼ PPI VERNAM | MO | 55/95 | | |
| | 5 IF | 6 PPI VERNAM | CN | 0/95 | | |
| | 2 PPI-TM | 4 PPI VERNAM | SOY | 30/60 | WG | 100/100 |
| 13 | 5 IF | 1¼ PPI VERNAM | WH | 50/90 | | |
| | 5 PPI-TM | 4 PPI VERNAM | SOY | 35/60 | WG | 100/100 |
| 14 | 5 IF | 6 PPI VERNAM | CN | 0/95 | | |
| | 5 PPI-TM | 4 PPI VERNAM | SOY | 35/60 | WG | 100/100 |
| 15 | 5 IF | 1¼ PPI VERNAM | MO | 50/100 | | |
| | 5 IF | 5 PPI VERNAM | CN | 50/90 | | |
| | 5 PPI-TM | 4 PPI VERNAM | SOY | 35/60 | WG | 100/100 |
| 16 | 5 IF | 6 PPI VERNAM | SOY | 20/60 | | |
| | 5 PPI-TM | 4 PPI VERNAM | SOY | 35/60 | WG | 100/100 |
| 17 | 5 PPI-TM | 4 PPI VERNAM | SOY | 40/60 | WG | 100/100 |
| 18 | 5 IF | 1¼ PPI VERNAM | MO | 50/100 | | |
| | 5 IF | 5 PPI VERNAM | CN | 65/95 | | |
| | | | SOY | 30/95 | | |
| 19 | 5 IF | 5 PPI VERNAM | CN | 80/95 | | |
| 20 | 5 IF | 1¼ PPI VERNAM | MO | 40/100 | | |
| | | | CN | 65/95 | | |
| 22 | 5 IF | 1¼ PPI VERNAM | MO | 50/100 | | |
| | 5 IF | 5 PPI VERNAM | CN | 70/95 | | |
| | | | SOY | 25/50 | | |
| 23 | 5 IF | 5 PPI VERNAM | SOY | 25/50 | | |
| 24 | 5 IF | 1¼ PPI VERNAM | MO | 50/100 | | |
| 26 | 5 IF | 5 PPI VERNAM | CN | 70/95 | | |
| 27 | 2 PPI-TM | 4 PPI TILLAM | SOY | 5/47 | WG | 95/95 |
| 28 | 5 IF | 1.25 PPI VERNAM | MO | 25/95 | | |
| | 5 IF | 5 PPI VERNAM | CN | 30/99 | | |
| 29 | 5 IF | 1.25 PPI VERNAM | MO | 25/95 | | |
| | 5 IF | 5 PPI VERNAM | CN | 50/99 | | |
| | 5 PPI-TM | 4 PPI VERNAM | SOY | 25/55 | WG | 95/95 |
| 30 | 5 IF | 1.25 PPI VERNAM | MO | 35/95 | | |
| | 5 IF | 5 PPI VERNAM | CN | 20/99 | | |
| | 4 PPI-TM | 4 PPI VERNAM | SOY | 15/55 | WG | 100/100 |
| | | | | | FT | 100/100 |
| 31 | 5 IF | 5 PPI VERNAM | CN | 10/99 | | |
| | 4 PPI-TM | 4 PPI VERNAM | SOY | 20/55 | | |
| 32 | 5 IF | 1.25 PPI VERNAM | MO | 95/95 | | |
| | 5 IF | 5 PPI VERNAM | CN | 20/99 | | |
| | 4 PPI-TM | 4 PPI VERNAM | SOY | 30/55 | | |
| 33 | 5 IF | 1.25 PPI VERNAM | MO | 25/95 | | |
| | 5 IF | 5 PPI VERNAM | CN | 45/99 | | |
| | 5 PPI-TM | 4 PPI VERNAM | SOY | 35/55 | WG | 95/95 |
| | 2 PPI-TM | 4 PPI VERNAM | SOY | 35/55 | WG | 100/100 |
| | | | | | FT | 100/100 |
| 34 | 5 IF | 1.25 PPI VERNAM | MO | 30/95 | | |

TABLE IV-continued

| Compound Number | Antidote Rate & Method | Herbicide Rate & Method | Crop | Result | Weed | Result |
|---|---|---|---|---|---|---|
|  | 5 IF | 5 PPI VERNAM | CN | 35/99 |  |  |
|  | 5 PPI-TM | 4 PPI VERNAM | SOY | 35/55 | WG | 95/95 |
| 35 | 5 IF | 1.25 PPI VERNAM | MO | 45/95 |  |  |
|  | 5 IF | 5 PPI VERNAM | CN | 20/99 |  |  |
|  | 5 PPI-TM | 4 PPI VERNAM | SOY | 30/55 | WG | 95/95 |
| 36 | 5 IF | 5 PPI VERNAM | SOY | 40/60 |  |  |
|  | 1 PPI-TM | 4 PPI VERNAM | SOY | 25/40 |  |  |
| 37 | 5 IF | 1.25 PPI VERNAM | MO | 70/95 |  |  |
| 38 | 5 IF | 1.25 PPI VERNAM | BA | 70/85 |  |  |
| 39 | 5 IF | 1.25 PPI VERNAM | MO | 30/95 |  |  |
|  |  |  | CT | 40/60 |  |  |
|  | 5 IF | 5 PPI VERNAM | CN | 25/90 |  |  |
| 40 | 5 IF | 5 PPI VERNAM | CN | 60/90 |  |  |
| 41 | 5 IF | 1.25 PPI VERNAM | MO | 20/95 |  |  |
|  | 5 IF | 5 PPI VERNAM | CN | 50/90 |  |  |
| 42 | 5 IF | 5 PPI VERNAM | CN | 70/90 |  |  |
| 43 | 5 IF | 1.25 PPI VERNAM | MO | 60/100 |  |  |
|  | 5 IF | 5 PPI VERNAM | SOY | 35/65 |  |  |
|  | 5 PPI-TM | 4 PPI VERNAM | SOY | 50/80 |  |  |
| 44 | 5 IF | 1.25 PPI VERNAM | MO | 35/97 |  |  |
|  | 5 IF | 5 PPI VERNAM | CN | 30/90 |  |  |
|  | 5 PPI-TM | 3 PPI RO-NEET | MO | 50/70 | WG | 50/100 |
| 45 | 1 PPI-TM | 2 PPI VERNAM | SOY | 50/80 | WG | 80/80 |
|  |  |  |  |  | FT | 55/55 |
|  |  |  |  |  | CB | 0/0 |
|  |  |  |  |  | MD | 25/25 |
| 46 | 5 PPI-TM | 4 PPI VERNAM | SOY | 45/55 |  |  |
| 47 | 5 IF | 1.25 PPI VERNAM | MO | 70/90 |  |  |
|  |  |  | RC | 65/95 |  |  |
|  | 5 IF | 5 PPI VERNAM | SOY | 45/60 |  |  |
| 48 | 5 IF | 1.25 PPI VERNAM | RC | 30/95 |  |  |
| 49 | 5 IF | 1.25 PPI VERNAM | MO | 20/90 |  |  |
|  | 5 IF | 5 PPI VERNAM | CN | 40/90 |  |  |
| 50 | 5 IF | 1.25 PPI VERNAM | RC | 60/95 |  |  |
|  | 5 IF | 5 PPI VERNAM | SOY | 40/60 |  |  |
| 51 | 5 IF | 1.25 PPI VERNAM | MO | 45/90 |  |  |
|  |  |  | BA | 30/90 |  |  |
|  | 5 IF | 5 PPI VERNAM | CN | 30/90 |  |  |
| 52 | 5 IF | 5 PPI VERNAM | SOY | 60/90 |  |  |
|  | 5 PPI-TM | 4 PPI VERNAM | SOY | 0/60 | WG | 100/100 |
|  | 1 PPI-TM | 2 PPI VERNAM | SOY | 10/20 | WG | 75/95 |
|  |  |  |  |  | FT | 60/77 |
|  |  |  |  |  | CB | 70/35 |
|  |  |  |  |  | SG | 20/50 |
|  | 2 PPI-TM | 4 PPI VERNAM | SOY | 0/43 | WG | 100/100 |
|  |  |  |  |  | FT | 100/100 |
|  |  |  |  |  | CB | 75/38 |
|  |  |  |  |  | SG | 100/73 |
| 53 | 5 PPI-TM | 4 PPI VERNAM | SOY | 40/55 | WG | 95/95 |
|  | 2 PPI-TM | 2 PPI VERNAM | SOY | 35/80 | WG | 80/80 |
|  |  |  |  |  | FT | 55/55 |
|  |  |  |  |  | MD | 25/25 |
|  | 4 PPI-TM | 2 PPI VERNAM | SOY | 0/80 | WG | 80/80 |
|  |  |  |  |  | FT | 55/55 |
|  |  |  |  |  | MD | 30/25 |
| 54 | 5 IF | 5 PPI VERNAM | SOY | 30/70 |  |  |
|  | 1 PPI-TM | 4 PPI VERNAM | SOY | 15/40 | WG | 100/100 |
| 55 | 5 IF | 5 PPI VERNAM | SOY | 30/70 |  |  |
| 56 | 5 IF | 5 PPI VERNAM | SOY | 40/70 |  |  |
|  | 2 PPI-TM | 4 PPI VERNAM | SOY | 25/40 | WG | 100/100 |
| 57 | 5 IF | 1.25 PPI VERNAM | RC | 70/90 |  |  |
|  | 5 IF | 5 PPI VERNAM | CN | 70/90 |  |  |
| 58 | 5 IF | 1.25 PPI VERNAM | MO | 65/95 |  |  |
|  |  |  | RC | 35/70 |  |  |
|  | 5 PPI-TM | 4 PPI VERNAM | SOY | 0/60 |  |  |
| 59 | 5 IF | 5 PPI VERNAM | SOY | 60/90 |  |  |
| 60 | 5 IF | 1.25 PPI VERNAM | MO | 75/90 |  |  |
| 61 | 5 IF | 1.25 PPI VERNAM | WH | 70/90 |  |  |
|  | 5 IF | 5 PPI VERNAM | SOY | 55/90 |  |  |
| 62 | 5 IF | 5 PPI VERNAM | SOY | 65/90 |  |  |
|  | 2 PPI-TM | 4 PPI VERNAM | SOY | 40/60 | WG | 100/100 |
| 63 | 5 IF | 1.25 PPI VERNAM | MO | 20/95 |  |  |
|  | 5 IF | 5 PPI VERNAM | CN | 40/90 |  |  |
|  |  |  | SOY | 55/90 |  |  |
|  | 5 PPI-TM | 4 PPI VERNAM | SOY | 25/60 | WG | 100/100 |
|  | 1 PPI-TM | 4 PPI VERNAM | SOY | 25/60 | WG | 100/100 |
| 64 | 5 IF | 1.25 PPI VERNAM | MO | 30/95 |  |  |
|  |  |  | WH | 35/90 |  |  |
|  |  |  | RC | 10/70 |  |  |
|  |  |  | BA | 30/80 |  |  |

TABLE IV-continued

| Compound Number | Antidote Rate & Method | Herbicide Rate & Method | Crop | Result | Weed | Result |
|---|---|---|---|---|---|---|
|  | 5 IF | 5 PPI VERNAM | CN | 30/90 |  |  |
| 65 | 5 IF | 1.25 PPI VERNAM | WH | 60/90 |  |  |
|  | 5 IF | 5 PPI VERNAM | SOY | 50/90 |  |  |
| 66 | 5 IF | 1.25 PPI VERNAM | MO | 45/97 |  |  |
|  | 5 IF | 5 PPI VERNAM | CN | 60/90 |  |  |
| 67 | 5 IF | 1.25 PPI VERNAM | MO | 40/97 |  |  |
|  | 5 IF | 5 PPI VERNAM | CN | 40/90 |  |  |
| 68 | 5 IF | 1.25 PPI VERNAM | MO | 15/97 |  |  |
|  | 5 IF | 5 PPI VERNAM | CN | 80/90 |  |  |
| 69 | 5 IF | 1.25 PPI VERNAM | MO | 30/97 |  |  |
|  | 5 IF | 5 PPI VERNAM | CN | 75/90 |  |  |
|  | 5 PPI-TM | 4 PPI VERNAM | SOY | 40/60 | WG | 100/100 |
| 70 | 5 IF | 1.25 PPI VERNAM | MO | 50/97 |  |  |
|  | 5 PPI-TM | 4 PPI VERNAM | SOY | 50/60 | WG | 100/100 |
| 71 | 5 IF | 5 PPI VERNAM | SOY | 50/60 |  |  |
|  | 5 PPI-TM | 4 PPI VERNAM | SOY | 40/55 | WG | 95/95 |
| 72 | 2 PPI-TM | 4 PPI VERNAM | SOY | 40/60 |  |  |
|  | 1 PPI-TM | 4 PPI VERNAM | SOY | 40/60 |  |  |
| 73 | 5 IF | 1.25 PPI VERNAM | MO | 60/95 |  |  |
|  | 5 IF | 5 PPI VERNAM | CN | 40/95 |  |  |
|  | 4 PPI-TM | 4 PPI VERNAM | SOY | 15/50 | WG | 100/100 |
|  | 1 PPI-TM | 4 PPI VERNAM | SOY | 10/50 | WG | 100/100 |
| 74 | 5 IF | 1.25 PPI VERNAM | MO | 35/95 |  |  |
|  |  |  | RC | 60/100 |  |  |
|  | 5 IF | 5 PPI VERNAM | CN | 35/95 |  |  |
|  |  |  | SOY | 15/60 |  |  |
|  | 5 PPI-TM | 4 PPI VERNAM | SOY | 20/40 | WG | 100/100 |
|  |  |  |  |  | FT | 100/100 |
|  | 1 PPI-TM | 4 PPI VERNAM | SOY | 25/40 | WG | 100/100 |
|  |  |  |  |  | FT | 100/100 |
| 75 | 5 IF | 1.25 PPI VERNAM | MO | 50/95 |  |  |
|  | 5 IF | 5 PPI VERNAM | CN | 35/95 |  |  |
|  | 4 PPI-TM | 4 PPI VERNAM | SOY | 20/50 | WG | 100/100 |
| 76 | 5 IF | 1.25 PPI VERNAM | MO | 60/95 |  |  |
|  | 5 IF | 5 PPI VERNAM | SOY | 25/60 |  |  |
|  | 5 PPI-TM | 5 PPI VERNAM | SOY | 30/60 | WG | 100/100 |
|  |  |  |  |  | FT | 85/85 |
| 77 | 5 IF | 1.25 PPI VERNAM | MO | 40/95 |  |  |
|  | 5 IF | 5 PPI VERNAM | SOY | 10/60 |  |  |
| 78 | 5 IF | 1.25 PPI VERNAM | MO | 60/95 |  |  |
|  |  |  | RC | 65/100 |  |  |
| 79 | 5 IF | 1.25 PPI VERNAM | MO | 40/95 |  |  |
|  | 5 IF | 5 PPI VERNAM | CN | 60/95 |  |  |
| 80 | 5 IF | 1.25 PPI VERNAM | MO | 40/95 |  |  |
|  | 5 IF | 5 PPI VERNAM | CN | 0/99 |  |  |
|  | 5 PPI-TM | 4 PPI VERNAM | SOY | 30/60 | WG | 100/100 |
| 81 | 5 PPI-TM | 4 PPI VERNAM | SOY | 15/50 |  |  |
| 82 | 5 IF | 5 PPI VERNAM | SOY | 30/60 | -- |  |
| 83 | 5 IF | 5 PPI VERNAM | CN | 0/90 |  |  |
|  |  |  | SOY | 40/65 |  |  |
| 84 | 5 IF | 5 PPI VERNAM | CN | 20/90 |  |  |
|  | 5 PPI-TM | 4 PPI VERNAM | SOY | 25/40 | WG | 100/100 |
|  |  |  |  |  | FT | 100/100 |
| 85 | 5 IF | 1.25 PPI VERNAM | MO | 60/100 |  |  |
|  | 5 IF | 5 PPI VERNAM | CN | 0/90 |  |  |
|  | 5 PPI-TM | 4 PPI VERNAM | SOY | 20/50 | WG | 85/85 |
|  | 2 PPI-TM | 4 PPI VERNAM | SOY | 20/50 | WG | 85/85 |
| 86 | 5 IF | 1.25 PPI VERNAM | MO | 60/100 |  |  |
|  | 5 IF | 5 PPI VERNAM | CN | 50/90 |  |  |
|  | 5 PPI-TM | 4 PPI VERNAM | SOY | 20/50 | WG | 85/85 |
|  | 2 PPI-TM | 4 PPI VERNAM | SOY | 30/50 | WG | 85/85 |
| 87 | 5 IF | 5 PPI VERNAM | CN | 0/90 |  |  |
|  | 5 PPI-TM | 4 PPI VERNAM | SOY | 30/50 | WG | 85/85 |
| 88 | 5 IF | 5 PPI VERNAM | CN | 15/90 |  |  |
|  | 5 PPI-TM | 4 PPI VERNAM | SOY | 25/50 | WG | 85/85 |
|  | 2 PPI-TM | 4 PPI VERNAM | SOY | 30/50 | WG | 85/85 |
| 89 | 5 IF | 5 PPI VERNAM | CN | 15/90 |  |  |
|  | 5 PPI-TM | 4 PPI VERNAM | SOY | 25/50 | WG | 85/85 |
| 90 | 5 IF | 5 PPI VERNAM | CN | 0/90 |  |  |
|  | 5 PPI-TM | 4 PPI VERNAM | SOY | 20/50 | WG | 85/85 |
| 91 | 5 IF | 5 PPI VERNAM | CN | 0/90 |  |  |
|  | 5 PPI-TM | 4 PPI VERNAM | SOY | 20/50 | WG | 85/85 |
| 92 | 5 IF | 5 PPI VERNAM | CN | 0/90 |  |  |
|  | 5 PPI-TM | 4 PPI VERNAM | SOY | 20/50 | WG | 85/85 |
| 93 | 5 IF | 5 PPI VERNAM | CN | 0/90 |  |  |
|  | 5 PPI-TM | 4 PPI VERNAM | SOY | 20/50 | WG | 85/85 |
| 94 | 5 IF | 5 PPI VERNAM | CN | 0/90 |  |  |
|  | 5 PPI-TM | 4 PPI VERNAM | SOY | 20/50 | WG | 85/85 |
|  | 2 PPI-TM | 4 PPI VERNAM | SOY | 25/50 | WG | 85/85 |
| 95 | 5 IF | 5 PPI VERNAM | CN | 20/90 |  |  |

TABLE IV-continued

| Compound Number | Antidote Rate & Method | Herbicide Rate & Method | Crop | Result | Weed | Result |
|---|---|---|---|---|---|---|
|  | 5 PPI-TM | 4 PPI VERNAM | SOY | 25/50 | WG | 85/85 |
| 96 | 5 IF | 5 PPI VERNAM | CN | 0/90 | | |
|  | 5 PPI-TM | 4 PPI VERNAM | SOY | 25/50 | WG | 85/85 |
|  | 1 PPI-TM | 4 PPI VERNAM | SOY | 25/50 | WG | 85/85 |
| 97 | 5 IF | 5 PPI VERNAM | CN | 0/90 | | |
|  | 2 PPI-TM | 4 PPI VERNAM | SOY | 25/50 | WG | 85/85 |
| 98 | 5 IF | 5 PPI VERNAM | CN | 0/90 | | |
|  | 5 PPI-TM | 4 PPI VERNAM | SOY | 25/50 | WG | 85/85 |
| 99 | 5 IF | 5 PPI VERNAM | CN | 0/90 | | |
|  | 5 PPI-TM | 4 PPI VERNAM | SOY | 20/50 | WG | 85/85 |
|  | 1 PPI-TM | 4 PPI VERNAM | SOY | 25/50 | WG | 85/85 |
| 100 | 5 IF | 5 PPI VERNAM | CN | 0/90 | | |
|  | 5 PPI-TM | 4 PPI VERNAM | SOY | 25/50 | WG | 85/85 |
|  | 1 PPI-TM | 4 PPI VERNAM | SOY | 30/50 | WG | 85/85 |
| 101 | 5 IF | 5 PPI VERNAM | CN | 0/90 | | |
|  | 2 PPI-TM | 4 PPI VERNAM | SOY | 25/50 | WG | 85/85 |
| 102 | 5 IF | 5 PPI VERNAM | CN | 0/90 | | |
|  | 2 PPI-TM | 4 PPI VERNAM | SOY | 30/50 | WG | 85/85 |
| 103 | 5 IF | 5 PPI VERNAM | CN | 0/90 | | |
|  | 2 PPI-TM | 4 PPI VERNAM | SOY | 25/50 | WG | 85/85 |
| 104 | 5 IF | 5 PPI VERNAM | CN | 0/90 | | |
|  | 5 PPI-TM | 4 PPI VERNAM | SOY | 35/50 | WG | 85/85 |
| 105 | 5 IF | 5 PPI VERNAM | CN | 0/90 | | |
|  |  |  | SOY | 10/65 | | |
|  | 5 PPI-TM | 4 PPI VERNAM | SOY | 30/50 | WG | 85/85 |
| 106 | 5 IF | 5 PPI VERNAM | CN | 0/90 | | |
|  | 5 PPI-TM | 4 PPI VERNAM | SOY | 25/50 | WG | 85/85 |
| 107 | 5 IF | 5 PPI VERNAM | CN | 0/90 | | |
|  | 5 PPI-TM | 4 PPI VERNAM | SOY | 35/50 | WG | 85/85 |
| 108 | 5 IF | 5 PPI VERNAM | CN | 0/90 | | |
| 109 | 5 IF | 1.25 PPI VERNAM | MO | 65/100 | | |
|  | 5 IF | 5 PPI VERNAM | CN | 0/90 | | |
| 110 | 5 IF | 1.25 PPI VERNAM | MO | 75/100 | | |
|  | 5 IF | 5 PPI VERNAM | CN | 0/90 | | |
| 111 | 5 IF | 5 PPI VERNAM | CN | 0/90 | | |
| 112 | 5 IF | 1.25 PPI VERNAM | MO | 65/100 | | |
|  | 5 IF | 5 PPI VERNAM | CN | 0/90 | | |
| 113 | 5 IF | 5 PPI VERNAM | CN | 0/90 | | |
|  |  |  | SOY | 40/65 | | |
| 114 | 5 IF | 5 PPI VERNAM | CN | 0/90 | | |
| 115 | 5 IF | 1.25 PPI VERNAM | BA | 55/85 | | |
|  | 5 IF | 5 PPI VERNAM | CN | 0/90 | | |
|  | 5 PPI-TM | 4 PPI VERNAM | SOY | 20/40 | WG | 90/90 |
| 116 | 5 IF | 1.25 PPI VERNAM | MO | 70/100 | | |
|  | 5 IF | 5 PPI VERNAM | CN | 70/90 | | |
| 117 | 5 IF | 5 PPI VERNAM | SOY | 30/40 | | |
| 118 | 5 IF | 5 PPI VERNAM | SOY | 25/50 | | |
| 119 | 5 IF | 1.25 PPI VERNAM | BA | 55/80 | — | |
| 120 | 5 IF | 1.25 PPI VERNAM | MO | 40/98 | | |
|  |  |  | BA | 45/80 | | |
|  | 5 IF | 5 PPI VERNAM | CN | 60/90 | | |
| 121 | 5 IF | 5 PPI VERNAM | SOY | 35/68 | | |
| 122 | 5 IF | 5 PPI VERNAM | SOY | 30/68 | | |
| 123 | 5 IF | 1.25 PPI VERNAM | MO | 55/93 | | |
|  | 5 IF | 5 PPI VERNAM | CN | 50/90 | | |
|  |  |  | SOY | 45/68 | | |
| 124 | 5 IF | 1.25 PPI VERNAM | MO | 50/93 | | |
|  | 5 IF | 5 PPI VERNAM | CN | 15/90 | | |
|  |  |  | SOY | 20/68 | | |
|  | 5 PPI-TM | 3 PPI VERNAM | SOY | 25/40 | | |
| 125 | 5 IF | 5 PPI VERNAM | SOY | 25/68 | | |
|  | 4 PPI-TM | 2 PPI VERNAM | SOY | 0/20 | WG | 90/90 |
|  |  |  |  |  | CB | 35/30 |
|  | 2 PPI-TM | 2 PPI VERNAM | SOY | 0/20 | WG | 90/90 |
|  |  |  |  |  | CB | 30/30 |
| 126 | 5 IF | 1.25 PPI VERNAM | MO | 40/100 | | |
|  |  |  | RC | 20/90 | | |
|  |  |  | BA | 10/95 | | |
|  | 5 PPI-TM | 1 PPI VERNAM | RC | 30/95 | WG | 90/90 |
|  | 1 PPI-TM | 1 PPI VERNAM | RC | 50/95 | WG | 90/90 |
|  | 4 PPI-TM | 3 PPI VERNAM | SOY | 20/40 | WG | 90/90 |
| 127 | 5 IF | 1.25 PPI VERNAM | CT | 20/40 | | |
|  | 5 IF | 5 PPI VERNAM | CN | 40/75 | | |
|  |  |  | SOY | 30/45 | | |
|  | 5 PPI-TM | 4 PPI VERNAM | SOY | 40/70 | WG | 100/100 |
|  |  |  |  |  | FT | 85/85 |
|  | 1 PPI-TM | 4 PPI VERNAM | SOY | 30/70 | WG | 100/100 |
|  |  |  |  |  | FT | 85/85 |
| 128 | 5 IF | 5 PPI VERNAM | CN | 0/75 | | |
|  |  |  | SOY | 20/45 | | |

TABLE IV-continued

| Compound Number | Antidote Rate & Method | Herbicide Rate & Method | Crop | Result | Weed | Result |
|---|---|---|---|---|---|---|
| | 5 PPI-TM | 4 PPI VERNAM | SOY | 40/70 | WG FT | 100/100 85/85 |
| | 1 PPI-TM | 4 PPI VERNAM | SOY | 40/70 | WG FT | 100/100 85/85 |
| 129 | 5 IF | 1.25 PPI VERNAM | MO | 70/100 | | |
| | 5 IF | 5 PPI VERNAM | CN | 50/75 | | |
| | | | SOY | 20/45 | | |
| | 5 PPI-TM | 4 PPI VERNAM | SOY | 30/70 | WG FT | 100/100 85/85 |
| | 2 PPI-TM | 4 PPI VERNAM | SOY | 35/70 | WG FT | 100/100 85/85 |
| | 4 PPI-TM | 3 PPI VERNAM | SOY | 30/40 | WG | 90/90 |
| 130 | 5 IF | 1.25 PPI VERNAM | BA | 30/95 | | |
| | 5 PPI-TM | 4 PPI VERNAM | SOY | 10/70 | WG FT | 100/100 85/85 |
| | 2 PPI-TM | 3 PPI VERNAM | SOY | 20/40 | WG | 90/90 |
| 131 | 5 IF | 5 PPI VERNAM | SOY | 40/65 | | |
| 132 | 5 IF | 5 PPI VERNAM | SOY | 30/60 | | |
| | 5 PPI-TM | 3 PPI VERNAM | SOY | 15/30 | WG | 90/90 |
| 133 | 5 IF | 1.25 PPI VERNAM | MO | 60/90 | | |
| | | | BA | 60/90 | | |
| 134 | 5 IF | 1.25 PPI VERNAM | RC | 20/70 | | |
| 135 | 5 IF | 1.25 PPI VERNAM | RC | 10/70 | | |
| | | | BA | 30/90 | | |
| 136 | 5 IF | 1.25 PPI VERNAM | MO | 50/90 | | |
| | | | RC | 25/70 | | |
| | | | BA | 30/90 | | |
| | 5 IF | 5 PPI VERNAM | SOY | 30/50 | | |
| | 5 PPI-TM | 3 PPI VERNAM | SOY | 15/40 | WG | 95/95 |
| | 2 PPI-TM | 3 PPI VERNAM | SOY | 15/40 | WG | 95/95 |
| 137 | 5 IF | 1.25 PPI VERNAM | MO | 40/90 | | |
| | | | WH | 45/75 | | |
| | | | BA | 25/90 | | |
| | 5 IF | 5 PPI VERNAM | CN | 45/90 | | |
| 138 | 5 IF | 1.25 PPI VERNAM | MO | 35/90 | | |
| | | | WH | 25/75 | | |
| | | | RC | 10/70 | | |
| | | | BA | 20/90 | | |
| 139 | 5 IF | 1.25 PPI VERNAM | MO | 55/90 | | |
| | 5 IF | 5 PPI VERNAM | SOY | 20/30 | | |
| 140 | 5 IF | 5 PPI VERNAM | SOY | 20/30 | | |
| | 5 PPI-TM | 3 PPI VERNAM | SOY | 20/40 | WG | 95/95 |
| 141 | 5 IF | 5 PPI VERNAM | SOY | 30/55 | | |
| 142 | 5 IF | 1.25 PPI VERNAM | BA | 40/65 | | |
| | 5 IF | 5 PPI VERNAM | SOY | 35/55 | | |
| 143 | 5 IF | 1.25 PPI VERNAM | MO | 60/100 | | |
| 144 | 5 IF | 1.25 PPI VERNAM | BA | 35/65 | | |
| 145 | 5 IF | 1.25 PPI VERNAM | CT | 35/45 | | |
| 146 | 5 IF | 5 PPI VERNAM | CN | 30/90 | | |
| | | | SOY | 40/60 | | |
| | 5 PPI-TM | 4 PPI VERNAM | SOY | 35/85 | WG | 95/95 |
| | 2 PPI-TM | 4 PPI VERNAM | SOY | 55/85 | WG | 95/95 |
| 147 | 5 IF | 5 PPI VERNAM | SOY | 30/60 | | |
| 148 | 5 IF | 1.25 PPI VERNAM | MO | 55/90 | | |
| | | | CT | 20/35 | | |
| 149 | 5 IF | 1.25 PPI VERNAM | MO | 65/90 | | |
| | 5 PPI-TM | 4 PPI VERNAM | SOY | 55/85 | WG | 95/95 |
| 150 | 5 IF | 5 PPI VERNAM | SOY | 20/60 | | |
| 151 | 5 IF | 5 PPI VERNAM | SOY | 35/60 | | |
| 152 | 5 IF | 5 PPI VERNAM | SOY | 35/60 | | |
| 153 | 5 IF | 1.25 PPI VERNAM | MO | 55/90 | | |
| | 5 IF | 5 PPI VERNAM | SOY | 15/60 | | |
| | 5 PPI-TM | 4 PPI VERNAM | SOY | 50/85 | WG | 95/95 |
| 154 | 5 IF | 5 PPI VERNAM | SOY | 55/75 | | |
| 155 | 5 IF | 5 PPI VERNAM | SOY | 15/60 | | |
| 156 | 5 IF | 5 PPI VERNAM | SOY | 40/60 | | |
| 157 | 5 IF | 1.25 PPI VERNAM | RC | 40/75 | | |
| | 5 IF | 5 PPI VERNAM | SOY | 30/60 | | |
| 158 | 5 IF | 1.25 PPI VERNAM | MO | 35/95 | | |
| | 5 IF | 5 PPI VERNAM | SOY | 40/60 | | |
| 159 | 5 IF | 1.25 PPI VERNAM | WH | 60/90 | | |
| | | | BA | 30/80 | | |
| | 5 IF | 5 PPI VERNAM | CN | 20/95 | | |
| 160 | 5 IF | 1.25 PPI VERNAM | MO | 25/90 | | |
| | 5 IF | 5 PPI VERNAM | CN | 25/95 | | |
| 161 | 5 IF | 5 PPI VERNAM | CN | 50/95 | | |
| | | | SOY | 40/65 | | |
| 162 | 5 IF | 1.25 PPI VERNAM | WH | 50/90 | | |
| | | | RC | 30/80 | | |
| | 5 IF | 5 PPI VERNAM | CN | 30/95 | | |

TABLE IV-continued

| Compound Number | Antidote Rate & Method | Herbicide Rate & Method | Crop | Result | Weed | Result |
|---|---|---|---|---|---|---|
|  |  |  | SOY | 30/65 |  |  |
| 163 | 5 IF | 5 PPI VERNAM | SOY | 45/65 |  |  |
| 164 | 5 IF | 5 PPI VERNAM | SOY | 30/65 |  |  |

KEY TO TABLE IV
Antidotes
Compound numbers in this table corresponds to the numbers and their chemical description in Table I.
Application:
IF = In-furrow surface
PPI-TM = Pre-plant incorporated of herbicide and anitdote as a tank mix
PPI = Pre-plant incorporation of herbicide or antidote as indicated
PES = Pre-emergence surface
ST = Seed treatment
Rates are shown in pounds per acre based on the surface area of the flat.
Reported result = Treated/untreated (T/U)

The antidote compounds and compositions of the present invention can be used in any convenient form. Thus, the antidote compounds can be formulated into emulsifiable liquids, emulsifiable concentrates, liquid, wettable powder, powders, granular or any other convenient form. In its preferred form, an herbicidal antidote compound in a non-phytotoxic quantity with respect to the crop is admixed with a selected herbicide and incorporated into the soil prior to or after planting the seed. It is to be understood, however, that the herbicides can be incorporated into the soil and thereafter the antidote compound can be incorporated into the soil. Moreover, the crop seed itself can be treated with a non-phytotoxic quantity of the compound and planted into the soil which has been treated with herbicides, or untreated with the herbicide and subsequently treated with the herbicide. The addition of the antidote compound does not effect the herbicidal activity of the herbicides except to render the activity selective with respect to beneficial crops.

The amount of antidote compound present can range between about 0.01 to about 30 parts by weight of antidote compound described herein per each part by weight of herbicide. The exact amount of antidote compound will usually be determined on economic ratios for the most effective amount usable. It is understood that a non-phytotoxic quantity of antidote compound with respect to a particular crop will be employed in the herbicidal compositions described herein.

Formulations

The compounds and compositions can be formulated in the same manner in which herbicides are generally formulated. The object of the formulation is to apply the compounds and compositions to the locus where control is desired by a conventional method. The "locus" may include soil, seeds, seedlings, and vegetation.

The active herbicidal ingredient of a formulation will generally be such that its application rate will be within the range of 0.01 to 50 lb/A (0.0112 to 56 k/ha). The antidote compound which may be formulated separately or together with the herbicide will generally comprise about 0.01 to about 30 parts by weight of the herbicide.

Formulations will generally contain several additives. Among these are some inert ingredients, diluent carriers, organic solvents, water, oil and water, water in oil emulsions, carriers of dusts and granules, and surface active wetting, dispersing, and emulsifying agents.

Fertilizers, e.g., ammonium nitrate, urea and superphosphate, may also be included.

Aids to rooting and growth, e.g., compost, manure, humus, sand, etc., may likewise be included.

Dusts are free-flowing powder compositions containing the herbicidal compound impregnated on a particulate carrier. The particle size of the carriers is usually in the approximate range of 30 to 50 microns. Examples of suitable carriers are talc, bentonite, diatomaceous earth, and pyrophyllite. Anti-caking and anti-static agents can be added, if desired. The composition generally contains up to 50% of active ingredient. Dusts, like liquid compositions, can be applied by spraying from boom and hand sprayers or airplanes.

Wettable powders are finely divided compositions comprising a particulate carrier impregnated with the herbicidal compound and additionally containing one or more surface active agents. The surface active agent promotes rapid dispersion of the powder in aqueous medium to form stable, sprayable suspensions. A wide variety of surface active agents can be used, for example, long chain fatty alcohols and alkali metal salts of the sulfated fatty alcohols; salts of sulfonic acid; esters of long chain fatty acids; and polyhydric alcohols, in which the alcohol groups are free, omega-substituted polyethylene glycols of relatively long chain length. A list of surface active agents suitable for use in agriculture formulations can be found in Wade Van Valkenburg, *Pesticide Formulations*, (Marcel Dekker, Inc., N.Y., (1973) at pages 79–84.

Granules comprise the herbicidal composition impregnated on a particulate inert carrier having a particle size of about 1 to 2 millimeters in diameter. The granules can be made by spraying a solution of the active ingredient in a volatile solvent onto the granule carrier. Suitable carriers in preparation of granules include clay, vermiculite, sawdust, granular carbon, etc.

The herbicidal compositions can also be applied to the soil in the form of a solution in a suitable solvent. Solvents frequently used in herbicidal formulations include kerosene, fuel oil, xylene, petroleum fractions with boiling ranges above xylene, and aromatic petroleum fractions rich in methylated naphthalenes.

Emulsifiable concentrates consist of an oil solution of the herbicide along with an emulsifying agent. Prior to use the concentrate is diluted with water to form a suspended emulsion of oil droplets. The emulsifiers used are usually a mixture of anionic and nonionic surfactants. Other additives such as spreading agents and stickers can be included in the emulsifiable concentrate.

The compounds and compositions of this invention can also be applied by addition to irrigation water supplied to the field to be treated. This method of applica-

What is claimed is:

1. Compounds having the formula

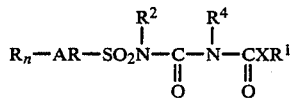

in which X is oxygen; n is an integer 0 to 3, inclusive;
R is lower alkyl having 1 to 4 carbon atoms, inclusive, lower alkoxy having 1–4 carbon atoms, inclusive, lower alkylthio having 1 to 4 carbon atoms, inclusive, halogen, trifluoromethyl, nitro, lower alkyl sulfonyl;
$R^4$ is hydrogen and lower alkyl having 1 to 4 carbon atoms, inclusive lower alkoxyalkyl having 2 to 6 carbon atoms, inclusive, phenyl and chlorophenyl;
$R^2$ is hydrogen, lower alkyl having 1 to 4 carbon atoms, alkoxyalkyl having 2–6 carbon atoms, and phenyl;
$R^1$ is lower alkyl having 1 to 4 carbon atoms, inclusive, alkenyl having 3 to 6 carbon atoms, inclusive, alkynyl having 3 to 6 carbon atoms, inclusive, haloalkyl having 1 to 4 carbon atoms, inclusive, alkoxyalkyl having 2 to 6 carbon atoms, inclusive, 1-phenyl propenyl, benzyl, chlorobenzyl, haloalkenyl having 3 to 6 carbon atoms, inclusive, phenyl and alkyl substituted phenyl wherein the alkyl moiety has 1 to 4 carbon atoms, inclusive; and
AR is phenyl, benzyl, naphthyl or styryl; and the inorganic base salts sodium, potassium, ammonium and other inorganic salts and organic base salts thereof selected from the group aniline, p-toluidine, benzylamine, allylamine, diallylamine, triallylamine, alkylamine, dialkylamine, trialkylamine, tetraalkyl ammonium, ethylaminoethyl, alkanolamine, dialkanolamine, trialkanolamine, quinoline, isoquinoline, ethylenediamine, benzyltrialkyl ammonium, choline, hydrazine, N,N-dialkyl hydrazine and tribenzylamine.

2. A compound according to claim 1 in which R is halogen, n is 1, 2 or 3, AR is phenyl, $R^4$ is hydrogen, $R^2$ is hydrogen, X is oxygen and $R^1$ is lower alkyl.

3. A compound according to claim 2 in which R is 4-chloro, and n is 1.

4. The compound according to claim 3 in which $R^1$ is methyl.

5. The compound according to claim 3 in which $R^1$ is ethyl.

6. The compound according to claim 3 in which $R^1$ is tertiary butyl.

7. The compound according to claim 3 in which $R^1$ is isopropyl.

8. The compound according to claim 2 in which R is 2,5-dichloro, n is 2 and $R^1$ is methyl.

9. The compound according to claim 2 in which R is 2-chloro, n is 1 and $R^1$ is methyl.

10. A compound according to claim 1 in which n is 0, AR is phenyl, $R^4$ is hydrogen, $R^2$ is hydrogen, X is oxygen and $R^1$ is lower alkyl.

11. The compound according to claim 10 in which $R^1$ is n-butyl.

12. The compound according to claim 10 in which $R^1$ is methyl.

13. A compound according to claim 1 in which R is lower alkyl, n is 1, 2 or 3, AR is phenyl, $R^4$ is hydrogen, $R^2$ is hydrogen, X is oxygen and $R^1$ is lower alkyl.

14. The compound according to claim 13 in which R is 4-methyl, n is 1 and $R^1$ is methyl.

15. The compound according to claim 13 in which $R^1$ is ethyl.

16. The compound according to claim 13 in which $R^1$ is isopropyl.

17. The compound according to claim 13 in which $R^1$ is tertiary butyl.

18. The compound according to claim 13 in which R is 2-methyl, n is 1 and $R^1$ is methyl.

19. A compound according to claim 1 in which R is trifluoromethyl, n is 1, AR is phenyl, $R^4$ is hydrogen, $R^2$ is hydrogen, X is oxygen and $R^1$ is lower alkyl.

20. The compound according to claim 19 in which R is 3-trifluoromethyl and $R^1$ is methyl.

21. A compound according to claim 1 in which R is nitro, n is 1, AR is phenyl, $R^4$ is hydrogen, $R^2$ is hydrogen, X is oxygen and $R^1$ is lower alkyl.

22. The compound according to claim 21 in which R is 3-nitro and $R^1$ is methyl.

23. The compound according to claim 21 in which R is 4-nitro and $R^1$ is methyl.

24. A compound according to claim 1 in which R is lower alkylthio, n is 1, AR is phenyl, $R^4$ is hydrogen, $R^2$ is hydrogen, X is oxygen and $R^1$ is lower alkyl.

25. The compound according to claim 24 in which R is 4-methylthio and $R^1$ is methyl.

26. A compound according to claim 1 in which R is lower alkoxy having 1–4 carbon atoms, inclusive, n is 1, AR is phenyl, $R^4$ is hydrogen, $R^2$ is hydrogen, X is oxygen and $R^1$ is lower alkyl having 1–4 carbon atoms, inclusive.

27. The compound according to claim 26 in which R is 4-methoxy and $R^1$ is methyl.

28. A compound according to claim 1 in which R is lower alkyl, n is 1, AR is phenyl, $R^4$ is lower alkyl, $R^2$ is hydrogen, X is oxygen and $R^1$ is lower alkyl.

29. The compound according to claim 28 in which R is 4-methyl, $R^4$ is methyl and $R^1$ is methyl.

30. The compound according to claim 28 in which R is 4-methyl, $R^4$ is ethyl and $R^1$ is methyl.

31. A compound according to claim 1 in which R is halogen, n is 1, AR is phenyl, $R^4$ is lower alkyl, $R^2$ is hydrogen, X is oxygen and $R^1$ is lower alkyl.

32. The compound according to claim 31 in which R is 4-chloro, $R^4$ is methyl and $R^1$ is methyl.

33. The compound according to claim 31 in which R is 4-chloro, $R^4$ is ethyl and $R^1$ is methyl.

34. A compound according to claim 1 in which R is lower alkyl having 1 to 4 carbon atoms, inclusive, lower alkoxy having 1 to 4 carbon atoms, inclusive, lower alkylthio having 1 to 4 carbon atoms, inclusive, halogen, trifluoromethyl, nitro or lower alkylsulfonyl and AR is phenyl, $R^4$ is hydrogen, $R^2$ is hydrogen, X is oxygen and $R^1$ is lower alkyl having 1 to 4 carbon atoms, inclusive, alkenyl having 3 to 6 carbons, inclusive, alkynyl having 3 to 6 carbon atoms, inclusive, haloalkyl having 1 to 4 carbon atoms, inclusive, haloalkenyl having 3 to 6 carbon atoms, inclusive, or alkoxyalkyl having 2 to 6 carbon atoms, inclusive.

35. A compound according to claim 1 in which R is lower alkyl having 1 to 4 carbon atoms, inclusive, lower alkoxy having 1 to 4 carbon atoms inclusive, lower alkylthio having 1 to 4 carbon atoms, inclusive, halogen, trifluoromethyl, nitro or lower alkylsulfonyl and AR is phenyl, $R^4$ is hydrogen, $R^2$ is hydrogen, X is oxygen and $R^1$ is benzyl, chlorobenzyl, phenyl, alkyl substituted phenyl wherein the alkyl moiety has 1 to 4 carbon atoms, inclusive, or 1-phenyl propenyl.

36. A compound according to claim 1 in which R is lower alkyl having 1 to 4 carbon atoms, inclusive, lower alkoxy having 1 to 4 carbon atoms, inclusive, lower alkylthio having 1 to 4 carbon atoms, inclusive, halogen, trifluoromethyl, nitro or lower alkylsulfonyl and AR is phenyl, $R^4$ is lower alkyl having 1 to 4 carbon atoms, inclusive, $R^2$ is hydrogen, X is oxygen and $R^1$ is lower alkyl having 1 to 4 carbon atoms, inclusive, alkenyl having 3 to 6 carbon atoms, inclusive, alkynyl having 3 to 6 carbon atoms, inclusive, haloalkyl having 1 to 4 carbon atoms, inclusive, haloalkenyl having 3 to 6 carbon atoms, inclusive, or alkoxyalkyl having 2 to 6 carbon atoms, inclusive.

37. A compound according to claim 1 in which R is lower alkyl having 1 to 4 carbon atoms, inclusive, lower alkoxy having 1 to 4 carbon atoms, inclusive, lower alkylthio having 1 to 4 carbon atoms, inclusive, halogen, trifluoromethyl, nitro or lower alkylsulfonyl and AR is phenyl, $R^4$ is lower alkyl having 1 to 4 carbon atoms, inclusive, $R^2$ is hydrogen, X is oxygen and $R^1$ is benzyl, chlorobenzyl, phenyl, alkyl substituted phenyl wherein the alkyl moiety has 1 to 4 carbon atoms, inclusive, or 1-phenyl propenyl.

* * * * *